United States Patent [19]

Labrie et al.

[11] Patent Number: 5,494,914
[45] Date of Patent: Feb. 27, 1996

[54] INHIBITORS FOR TESTOSTERONE 5α-REDUCTASE ACTIVITY

[75] Inventors: Fernand Labrie; Yves M. Mérand; Shankar M. Singh, all of Ste-Foy, Canada

[73] Assignee: Endorecherche, Canada

[21] Appl. No.: 196,332

[22] Filed: Feb. 14, 1994

Related U.S. Application Data

[62] Division of Ser. No. 886,961, May 21, 1992, abandoned.
[51] Int. Cl.$^6$ ............................................. A61K 31/44
[52] U.S. Cl. ........................... 514/284; 514/859; 514/864
[58] Field of Search ................................... 514/284, 859, 514/864

[56] References Cited

U.S. PATENT DOCUMENTS

| | | | |
|---|---|---|---|
| 3,001,988 | 9/1961 | Nysted | 260/399.55 |
| 3,300,523 | 1/1967 | Brown | 260/397.4 |
| 3,995,060 | 11/1976 | Neri et al. | 424/324 |
| 4,024,248 | 5/1977 | Konig et al. | 424/177 |
| 4,055,641 | 10/1977 | Benson et al. | 424/242 |
| 4,087,461 | 5/1978 | Robinson | 260/586 E |
| 4,100,274 | 7/1978 | Dutta et al. | 424/177 |
| 4,118,483 | 10/1978 | Konig et al. | 424/177 |
| 4,139,638 | 2/1979 | Neri et al. | 424/324 |
| 4,161,540 | 7/1979 | Neri et al. | 424/324 |
| 4,191,759 | 3/1980 | Johnston et al. | 514/179 |
| 4,220,775 | 9/1980 | Rasmusson et al. | 546/77 |
| 4,235,893 | 11/1980 | Brodie et al. | 424/243 |
| 4,329,364 | 5/1982 | Neri et al. | 424/324 |
| 4,377,584 | 3/1983 | Rasmusson | 424/258 |
| 4,386,080 | 5/1983 | Crossley et al. | 424/209 |
| 4,472,382 | 9/1984 | Labrie et al. | 424/177 |
| 4,481,190 | 11/1984 | Nestor et al. | 424/177 |
| 4,547,493 | 10/1985 | Teutsch et al. | 514/179 |
| 4,634,696 | 1/1987 | Teutsch et al. | 514/179 |
| 4,659,516 | 4/1987 | Bowler et al. | 260/397.5 |
| 4,659,695 | 4/1987 | Labrie | 514/15 |
| 4,732,912 | 3/1988 | Pilgrim et al. | 514/510 |
| 4,751,240 | 6/1988 | Bowler et al. | 514/510 |
| 4,760,053 | 7/1988 | Labrie | 514/15 |
| 4,760,061 | 7/1988 | Edwards et al. | 514/211 |
| 4,822,528 | 4/1989 | Columbo et al. | 260/397.3 |
| 4,859,681 | 8/1989 | Rasmusson et al. | 514/284 |
| 4,904,661 | 2/1990 | Pilgrim et al. | 514/237.5 |
| 4,937,237 | 6/1990 | Holt et al. | 514/75 |
| 5,021,414 | 6/1991 | Pilgrim et al. | 514/237.5 |
| 5,023,234 | 6/1991 | Labrie | 514/15 |
| 5,026,882 | 6/1991 | Holt et al. | 552/506 |
| 5,053,403 | 10/1991 | Orentreich et al. | 514/170 |
| 5,061,801 | 10/1991 | Williams et al. | 546/77 |
| 5,061,802 | 10/1991 | Steinberg et al. | 546/77 |
| 5,061,803 | 10/1991 | Williams | 546/77 |
| 5,064,813 | 11/1991 | Labrie | 514/15 |
| 5,204,337 | 4/1993 | Labrie | 514/182 |
| 5,237,064 | 8/1993 | Bakshi et al. | 546/14 |

FOREIGN PATENT DOCUMENTS

| | | |
|---|---|---|
| 10669/88 | 7/1988 | Australia. |
| 10778/88 | 8/1988 | Australia. |
| 31569/89 | 9/1989 | Australia. |
| 0855992 | 10/1977 | Belgium. |
| 0970692 | 7/1975 | Canada. |
| 052799 | 10/1981 | European Pat. Off.. |
| 58481 | 8/1982 | European Pat. Off.. |
| 0314199 | 2/1985 | European Pat. Off.. |
| 0155096 | 2/1985 | European Pat. Off.. |
| 138504 | 4/1985 | European Pat. Off.. |
| 160508 | 11/1985 | European Pat. Off.. |
| 163416 | 12/1985 | European Pat. Off.. |

(List continued on next page.)

OTHER PUBLICATIONS

Voigt et al., Endo, (1973), 92(4), pp. 1216–1922.
Green et al., Nature, 320(13) Mar. 1986, pp. 134–139.
Lubahn et al., Science, (1988) 240 pp. 327–330.
Lubahn et al. Proc. Natl Acad. Sci. USA 86, 9534–9538, Dec. 1989.
Neri et al., J. Steroidal Biochem., 1975, (6), pp. 815–819.
Chang, et al., Biochemistry, 1982, 21(17) 4302–4109.
Gyorki, et al., J. Steroidal Biochem. 25(3), 355–358, 1986.
Macaulay, et al., J. Steroidal Biochem. 26(5) 535–538, 1987.
Grunwell, et al., Steroids, 27(6), 1976, pp. 759–771.
Chin, et al., J. Biol. Chem., 250(19), 1975, pp. 1682–1686.
Auchus et al., Biochemistry, 1986, 25, 7295–7300.
Schwarz, Organic Synthesis Collective, vol. 3: 332–333 (1955).
Cooke, Jr.., Tetrahedron Letters, 22 pp. 1983–1986, 191.
Gibson, et al., Angew Chem. Int. Ed. 7 (1968) No. 12, pp. 919–930.
Raucher, et al., J. Org. Chem., 1981, 46, 3558–3559.
Weiss, et al., Angew Chem. Int. Ed. 12 (1973) No. 10, p. 841.
Bull, et al., Chem. Soc. Chem. Commun. 1986, pp. 451–453.
Wang, et al., Can J. Chem., 65, 2121–2131, 1987.
Jordan, et al., Endocrinology, 124 (4), 1989, pp.

1717–1726.

(List continued on next page.)

*Primary Examiner*—Kimberly Jordan
*Attorney, Agent, or Firm*—Ostrolenk, Faber, Gerb & Soffen

[57] ABSTRACT

Inhibitors of testosterone 5α-reductase activity, for example those of formula:

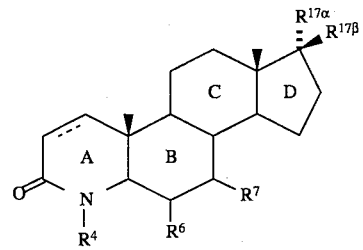

wherein novel substituents are provided at the $R^4$, $R^6$, $R^7$, $R^{17\alpha}$ and/or $R^{17\beta}$ positions are useful for the treatment of diseases whose progress is aided by activation of androgen receptors, e.g., prostate cancer, benign prostatic hyperplasia, acne, seborrhea, hirsutism, androgenic alopecia and the like.

38 Claims, No Drawings

OTHER PUBLICATIONS

Musto, et al., Endo. Res. Comm. (1977), vol. 4, No. 2, pp. 141–158.
Solo, et al., Steroids, vol. 40, No. 6 (1982), pp. 603–614.
De Larminat, et al., The Prostate, vo. 5 (1984), pp. 123–140.
Beardwell, et al., (1983) Cancer Chemother. Pharmacol. 10, No. 3, 158–160.
Brooks, et al., (1982) The Prostate, 3, No. 1, 35–44.
Bruchovsky, et al., (1968) J. Biol. Chem. 243, No. 8, 2012–2021.
Coy, et. al., (1982) Endocrinology, 110, 1445–1447.
Debruyne, F. (1988) Bailliere's Clin. Oncol. Int'l. Practice & Res., pp. 559–570.
Gohring et al., World Patent Information, vol. 11, No. 1., pp. 5–10, 1988.
Salman, et al., J. Steroid Biochem, vol. 33, No. 1, pp. 25–31 (1989).
Lefebvre, et al. Prostate 1982, 3(6), 569–578.
Lee et al., Steroids 22, 677–685, 1973.
Mobbs, et al., 71th An. Meeting of the Endocrine Soc., No. 1410, 1989.
Mobbs et al., J. Steroidal Biochem., 19(3), 1279–1290, 1983.
Donnelly, "Continuous Subcutaneous Administration of 'Zoladex' (ICI 118,630—An LH–RH Analogue) to Patients with advanced Prostatic Cancer", ICI Pharmaceuticals Division, Macclesfield, U.K., 1988.
Tora, et al. EMBO 8(7) 1981–1986, 1989.
Nayfeh, et al., Steroids 14:3, 1969, pp. 269–283.
Luthy, et al., J. Steroid Biochem. 31(5) 845–52, 1988.
Labrie, et al., The Prostate, 4, 579–594, 1983.
Begin, et al., Molecular and Cellular Endocrinology, 58 (1988) 213–219.
Lee et al., J. Androl. 2(6) 293–299, 1981.
Belis et al., J. Androl. 4, 144–149, 1983.
Schally, et al., Cancer Treatment Reports, 68(a), 281–288 (1984).
Levesque, et al., J. Med. Chem. 1991, 34 1624–1630.
Santen, et al. LHRH and Its Analogues, MTP Press, pp. 351–364, (1984).
Labrie et al., J. Steroid Biochem. 19(1) 999–1007, 1983.
Labrie, et al., (1984) 7th International Congress of Endocrinology 1984, p. 98.
Lambert, et al., (1986) Ann. Clin. Biochem., 23, 225–229.
Potts, et al., (1978) Steroids, 32, No. 2, 257–267.
Wilson, J. (1975) Handbk of Physio., Sec. 7, Endo. V, Amer. Physio. Soc. pp.491–508.
Farnsworth, W. E. (1969) Investigative Urology, 6, No. 4, 423–427.
Groom, et al., (1971) Biochem. J., 122, 125–126.
Geller, et al., (1989) 71st Ann. Endo. Soc. Meet. (Seattle, 6/21–24). No. 1640, p. 432.
Gormley, et. al., (1989) 71st Ann. Endo. Soc. Meet. (Seattle, 6/21–24). No. 1225, p. 329.
Wagner, et al., (1975) Acta Endocr. (Kbh), Suppl. 193, 52 (abst).
Robinson, et al., (1984) J. Steroid Biochem., 21, No. 5, 601–605.
Swaneck, et al., (1982) Biochem. Biophysical Res. Comm., 106, No. 4, 1441–1447.
Petrow, et al., (1982) J. Endocr., 95, 311–313.
Kadohma, et al., (1985) J. Natl. Cancer Inst., 74, No. 2, 475–486.
Earnshaw, et al., (1984) Clin. Invest., 21, 13–21.
Corbin, et al., (1984) J. Steroid Biochem., 20 (6B), 1369, No. A9.
Dutta et al., (1978) J. Med. Chem., 21, No. 10, 1018–1024.
Erchegyi, et al., (1981) Blochem. & Biophysical Res. Comm. 100, No. 3, 915–920.
Nestor, et al., (1984) J. Steroid Blochem., 20 (6B), 1366, No. A3.
Faure, et al., LHRH and Its Analogs, pp. 337–349, 1988.
Walsh, et al., The Journal of Clinical Investigation, vol. 57, Apr. 1976, pp. 1093–1097.
Brooks, et al. Proc. of the Soc. for Exp. Biology and Medicine, 169, 67–73 (1982).
George, et al., "The Effect of A 5-α-Reductase Inhibitor on Androgen Physiology in the Prepubertal Male Rat", 1165, Department of Cell Biology and Anatomy, University of Texas Southwestern Medical Center, Dallas, TX 75235, 1988.
Tenover, et al., "Effects of 24–Week Administration of a 5α–Alpha Reductase Inhibitor (MK–906) on Serum Levels of Testosterone (T), Free T, and Gonadotropins in Men", 583, Department of Medicine, University of Washintton, Seattle, WA 98103, 1988.
Liang, et al., Endocrinology, vol. 112, No. 4, pp. 1460–1468, 1988.
Sharpless, et al., *Tetrahedron Letters*, 1979 (1973).
Riess, Institut de Chimie. Strasbourg, France (Jul. 31, 1964).
Fujimoto, *J. Pharm. Soc. Jap*, 87:270 (1967).
Toth, et al. (1982) *J. Steroid Biochem* 17:653–660.
Junkmann, K. (1957) *Recent Progr. Horm. Res.*, 13:1389–1427.
Weinbauer, et al. (1986) *Acta Endocrinologica* 113:128–132.
Séguin, et. al. *Mol. Cell. Endocrinol.*, 21, 37–41 1981.
Neumann et al., *In: Clinics in Oncology*, vol. 1, pp. 41–64, 1982.
Simard, et al., *Mol. Cell. Endocrinol.*, 44, 261–270, 1986.
Poyet and Labrie, *Mol. Cell. Endocrinol.*, 42, 283–288, 1985.
Furr, et al. *J. Endocr.*, 113, R7–R9, 1987.
Labrie, et al., *Important Advances in Oncology*, Philadelphia, pp. 193–217, 1985.
Wakeling, et al. *J. Endocr.*, 112, R7–R10, 1987.
Wakeling, et al. *J. Steroid Biochem.*, 30, 141–147, 1987.
Bhatnager, et al. *Biol. Chem.* 253, 811–815, 1978.
Chin, et al. *J. Biol. Chem.*, 255, 3660–3664, 1980.
Thomas, et al. *J. Biol. Chem.*, 258, 1587–1590, 1983.
Tobias, et al. *J. Biol. Chem.*, 257, 2783–2786, 1982.
Thomas, et al. *J. Biol. Chem.*, 258, 11500, 1983.
Labrie, et al. *Endocrinology* 123: 1412–1417, 1988.
Plante, et al., *J. Steroid Biochem.*, 31(1), 61–64 (1988).
Rivier, et al., LHRH Analogs as Antiovulatory Agents, pp. 11–22, 1988.
Nestor, Jr. et al., LHRH Agonists & Antagonists Containing . . . Amino Acids, pp. 23–33, 1988.
Salman, et al., *J. Steroid Biochem.*, 26, 383–391, 1987.
Habenicht, et al., (1987) The Prostate, 11, 313–326.
DeKlerk, et al., (1985), The Prostate, 7, 1–12.
Redding, et al., (1983) Proc. Natl. Acad. Sci. USA, 80, 1457–1462.
Kerle, et al., (1984) J. Steroid Biochem. 20 (6B), 1395, No. A61.
Stewart, et al., (1969) In: Solid Phase Peptide Synthesis, Freeman and Co, San Francisco.

Coy, et al. (1976) J. Med. Chem., 19, No. 3, 423–425.
Wenderoth, et al., (1983) Endocrinology, 113, No. 2, 569–573.
McConnell, et al., (1989) The Journal of Urology, 141, 239A, No. 280.
Stoner, E. (1989) Lecture: Role of 5α-reductase inhibitor in BPH. AUA Today, Nov./Dec.
Toomey, et al. (1989) 71st Ann. Endo. Soc. Meet. (Seattle, 6/21–24). No. 1226, p. 329.
Labrie, et al. (1987) J. Steroid Biochem., 28, No. 4, 379–384.
Simard, et al., (1988) Molecular Endocrinology, 2, No. 9, 775–784 pp. 3–10.
Moore, et al., (1979) J. Clin. Invest., 63, 351–357.
Nestor, J. (1984) Devel. of agon. LHRH analogs, *LHRH & its analogs*, MTP Press Ltd.
Williams, et al. (1987) Cancer Treatment Reports, 71, No. 12, 1197–1201.
Chan, et al., (1987) Biochemical Biophysical Research Communication, 144 (1) 166–171.
Taylor, M. J. (1987) J. Endocr., 113, 489–493.
Rivier, et al., (1984) J. Steroid Biochem., 20 (6B), 1365, No. A1.
Labrie, et al., 157–200, Genitourinary Cancer. ISBN 0-89838-830-9 (1987).
Stoner, E., *J. Steroid Biochm. Molec. Biol.*, vol. 37, No. 3, pp. 375–378 (1990).
Dorrenbos, N. J., et al., *J. Pharm. Sci.*, 63: 620–21 (1974).
"The Merck Index", PROSCAR (1989) p. 1250.
Dorrenbos, N. J., Solomons, W. E., *J. Pharm. Sci.*, 62:638–640 (1973).
Kadohama, et al., *Cancer Res.*, 44:4947–4954 (1984).
Lan–Hargest, et al., *Tetrahedron Letters*, 28: 6117–6120 (1987).
Liang, T., et al., *J. Steroid Biochem.*, 256: 7998–8005 (1981).
MacIndoe, et al., *J. Steroid Blochem.*, 20: 1095–1100 (1984).
Nakayama, et al., *J. Antibiotics*, XLII: 1235–1240 (1989).
Nakayama, et al., *J. Antibiotics*, XLII: 1230–1234 (1989).
Nakayama, et al., *J. Antibiotics*, XLII: 1221–1229 (1989).
Petrow, et al., *Steroids*, 38:121–140 (1981).
Petrow, et al., *J. Steroid Biochem.*, 19:1491–1502 (1983).
Solomons, et al., *J. Pharm. Sci.*, 63:19–23 (1974).
Andersson, et al., *Nature*, 354, pp. 159–161 (1991).
Vermeulen, et al., *The Prostate* 14, pp. 45–53 (1989).
di Salle, et al., "17β-Acylurea Derivatives of 4-Azasteroids as inhibitors of Testosterone 5α-Reductase", 1988.
Weintraub, et al., *J. Med. Chem.*, 28:831–833 (1985).
Rasmusson, et al., *J. Med. Chem.* 1986, 29, pp. 2298–2315.
Rasmusson, et al., *J. Med. Chem.*, 1984, 27, pp. 1690–1701.
Brooks, et al., *Steroids* 47/1, 1986 pp. 1–19.
Levy, et al., *Biochemistry* 1990, vol. 29, pp. 2815–2824.
Levy, et al. *J. Steroid Blochem*, vol. 34, Nos. 1–6, pp. 571–575, 1989.
Holt, et al., *J. Med. Chem.*, 1990, vol. 33 pp. 937–942.
*DIALOG Information Services*; Biological abstracts retrieved 19 Jun. 1990; pp. 21 and 32.
Metcalf, et al. *TiPS*; Dec. 1989 vol. 10 pp. 491–495.
Rittmaster, et al., *J. Clin. Endo. and Metabolism*, vol. 65, No. 1 (1987) pp. 188–193.
Brooks, et al., *Endocrinology*, (1961) vol. 109, No. 3, pp. 830–836.
Andersson, et al., *Proc. Natl. Acad. Sci. USA*, vol. 87, pp. 3640–3644 (1990).
Liang, et al., *Endocrinology*; 1985, vol;. 117, No. 2, pp. 571–579.
Anderson, et al., *Nature*, vol. 219, Jul. 20, 1968, pp. 277–279.
Liang, et al., *J. Bio. Chem.*, vol. 259, No. 2 pp. 734–739 (1984).
Imperato–McGinley, et al., Abst. 1639 Comparison of Plasma & Urinary . . . Deficiency, 1988.
Doorenbos, et al., *Chemistry and Industry*, Oct. 1970, p. 1322.
Doorenbos, et al., *J. of Pharm. Sciences*, vol 60, No. 8, (1971) pp. 1234–1235.
Metcalf, et al., *Tetrahedron Letters*, vol. 21, pp. 15–18 (1980).
STN International US Pat. Abs. 4,882,319 (pp. 6–7), 1988.
Abstract of European Patent Appln. 294035, 1988.
STN International; Abstract of U.S. Pat. No. 4,396,615, 1980.
STN International; Abstract of European Patent Application No. 343,954, 1988.
STN International; Abstract of British Patent No. GB 2,048,888, 1988.
STN International; Abstract of U.S. Pat. No. 4,317,817, 1979.
STN International; Abstract of European Patent No. 289327, 1988.

FOREIGN PATENT DOCUMENTS

| | | |
|---|---|---|
| 0200859 | 11/1986 | European Pat. Off. . |
| 0271219 | 11/1987 | European Pat. Off. . |
| 0277002 | 1/1988 | European Pat. Off. . |
| 166509 | 1/1988 | European Pat. Off. . |
| 0294937 | 5/1988 | European Pat. Off. . |
| 298652 | 6/1988 | European Pat. Off. . |
| 0271220 | 6/1988 | European Pat. Off. . |
| 0285383 | 10/1988 | European Pat. Off. . |
| 375351 | 12/1989 | European Pat. Off. . |
| 375347 | 6/1990 | European Pat. Off. . |
| 375349 | 6/1990 | European Pat. Off. . |
| 414491 | 8/1990 | European Pat. Off. . |
| 414490 | 8/1990 | European Pat. Off. . |
| 414529 | 8/1990 | European Pat. Off. . |
| 427434 | 5/1991 | European Pat. Off. . |
| 435321 | 7/1991 | European Pat. Off. . |
| 458207 | 11/1991 | European Pat. Off. . |
| 1465544 | 1/1967 | France . |
| 7022461 | 6/1970 | France . |
| 0883091 | 5/1980 | France . |
| 2529969 | 1/1976 | Germany . |
| 3339295 | 5/1984 | Germany . |
| 83545 | 10/1981 | Luxembourg . |
| 137542 | 9/1967 | New Zealand . |
| 142112 | 6/1968 | New Zealand . |
| 123341 | 9/1970 | New Zealand . |
| 181107 | 11/1978 | New Zealand . |
| 182661 | 7/1979 | New Zealand . |
| 201536 | 8/1982 | New Zealand . |
| 206745 | 1/1984 | New Zealand . |
| 207413 | 11/1984 | New Zealand . |
| 211145 | 2/1985 | New Zealand . |
| 213652 | 9/1985 | New Zealand . |
| 222883 | 12/1987 | New Zealand . |
| 208441 | 1/1988 | New Zealand . |
| 214798 | 9/1988 | New Zealand . |
| 214998 | 6/1989 | New Zealand . |
| 223262 | 8/1989 | New Zealand . |
| 222103 | 8/1989 | New Zealand . |
| 237023 | 2/1991 | New Zealand . |
| 8601105 | 2/1986 | WIPO . |
| 8705216 | 9/1987 | WIPO . |
| 9100732 | 1/1991 | WIPO . |
| 9112261 | 8/1991 | WIPO . |
| 9113060 | 9/1991 | WIPO . |

INHIBITORS FOR TESTOSTERONE 5α-REDUCTASE ACTIVITY

This is a divisional of U.S. patent application Ser. No. 07/886,961, filed May 21, 1992 now abandoned.

FIELD OF THE INVENTION

This invention relates to pharmaceutical compositions and methods for the treatment of androgen-related diseases, said compositions having novel inhibitors of testosterone 5α-reductase activity. The inhibitors have a good combination of inhibitory effect on 5α-reductase activity, low or no androgenic activity and, in some embodiments, antiandrogenic activity. More particularly, certain embodiments of the invention relate to derivatives of 4-aza-androstanone or 4-aza-androstenone.

BACKGROUND OF THE INVENTION

Prior art inhibitors of 5Oα-reductase fail to provide an optimal combination of (1) lack of inherent androgenic activity and (2) ability to inhibit both of two different forms of testosterone 5α-reductase ("5α-reductase").

5α-reductase is an enzyme which catalyzes the conversion of the androgen, testosterone, to the much more potent androgen dihydrotestosterone ("DHT"). DHT is the more active androgen in many target organs (Anderson and Liao. Nature 219:277–279, 1968). The same enzyme catalyzes the conversion of androstenedione into androstanedione. Inhibitors of 5α-reductase inhibit biosynthesis of the products whose formation is catalyzed by 5α-reductase.

5α-reductase has been studied in different species (Liang et al. Endocrinology 117: 571–579, 1985). Its isolation and structure, and the expression of cDNA encoding it have been described (Andersson and Russell. Proc. Natl. Acad. Sci. 87:3640–3644, 1990).

Recent data have demonstrated the presence of at least two different genes expressing 5α-reductase in humans. Type I 5α-reductase (Andersson and Russell, Proc. Natl. Acad. Sci. 87, 3640–3644, 1990) is expressed at a low level in the human prostate while type II 5α-reductase is the predominant enzyme isoform expressed in this tissue (Andersson et al., Nature 354, 159–161, 1991).

The blockade of 5α-reductase has been intensively studied in view of developing pharmaceutical drugs for the therapy of diseases, such as prostate cancer. In European Patent Appln. No. EP 285 383 Ramusson et al. disclose the treatment of prostatic carcinoma with 17β-N-monosubstituted-carbamoyl-4-aza-5α-androst-1-en-3-ones). Diseases for which 5Oα-reductase inhibitors are also being studied include acne, baldness (Rittmaster et al. J. Clin. Endocrinol. Metab. 65: 188–193, 1987) and benign prostatic hyperplasia (Metcalf et al., TiPS 10: 491–495, 1989).

The 4-aza-steroid N,N-diethyl-4-methyl-3-oxo-4-aza-5α-androstane-17β-carboxamide, 4-MA has proven useful in inhibiting the formation of DHT from testosterone in rat prostate in vitro and in vivo (Brooks et al. Endocrinology 109: 830–836, 1981), thus reducing the testosterone-induced increase in ventral prostate weight in these animals. Another 4-aza-steroid, MK-906 (PROSCAR), has been found to cause a reduction in the intraprostatic concentration of DHT and a 25–30% reduction in prostatic size in men (Imperato-McGinley et al., Proc. 71st Ann. meet. Endocr. Soc., p. 332, abst 1639, 1989). However, Proscar is reported to be a potent inhibitor of the type II enzyme but a weak inhibitor of the type I enzyme (Andersson et al., Nature 354, 159–161, 1991). Such a low inhibitory potency on type I 5α-reductase probably explains why the highest doses of Proscar used in men generally fails to reduce serum dihydrotestosterone levels below 25 to 35% of control, thus leaving a highly significant concentration of circulating androgens (Vermeulen et al., The Prostate 14, 45–53, 1989). The inhibitory effect of the drug on prostatic volume in men remains limited at 25 to 35% over a period of 6 months (Stoner, J. Steroid Biochem. Mol. Biol. 37, 375–378, 1990). There is thus a need to develop compounds which can efficiently inhibit both type I and type II 5α-reductase and thus cause a more complete inhibition of circulating dihydrotestosterone levels. In U.S. Pat. No. 4,317,817, Belgian Patent Application No. 883 091 and British Patent Application. No. 204 8888, Blohm and Metcalf discuss the use of certain diazo-steroids as steroid 5α-reductase inhibitors. Metcalf et al describe the synthesis of related compounds in Tetrahedron Lett. 21, 15–18, 1980.

In EP Publication No. 343 954, EP Publication No. 375.347, U.S. Pat. No. 4,882,319, U.S. Pat. No. 4,937,237 and J. Med. Chem. 33: 937–942, 1990, Holt et al. discuss the use of certain A-ring aryl steroid derivatives as steroid 5Oα-reductase inhibitors.

In EP Publication No. 289 327 and Publication No. 427 434, on one hand, and in J. Steroid Biochem. 34: 571–575, 1989 and Biochemistry 29: 2815–2824, 1990, on the other hand, Holt and Levy discuss, respectively, the use of androstene- and pregnene-3-carboxylate derivatives as steroid-5α-reductase inhibitors.

In EP Publication No. 375 351, Holt et al. discuss the preparation of phosphoric acid substituted steroids as testosterone 5α-reductase inhibitors.

In EP Publication No. 271 219, EP Publication No. 314 199, and EP Publication No. 155 096, Rasmusson and Reynolds discuss the preparation of 17β-substituted-4-aza-5α-androstenones as steroid-5α-reductase inhibitors.

Brooks, et al. (Steroid 47: 1–19, 1986; Prostate 9: 65–76, 1986) have reported 5α-reductase inhibiting and androgen-blocking activities for some 4-aza-steroids.

Rasmusson et al. discuss certain aza-steroids as inhibitors of rat prostatic 5Oα-reductase (in J. Med. Chem. 27: 1690–1701, 1984; idem 29: 2298–2315, 1986 and J. Biol. Chem. 259: 734–739, 1984).

In EP Publication No. 277 002, Holt et al. discuss 17β-substituted-4-aza-5α-androstane-3-ones.

In EP Publication No. 271 220, Carlin et al. discuss the preparation of 17β-(N-monosubstituted carbamoyl)-4-aza-5α-androstane-3-ones.

In EP Publication No. 200 859, Cainelli et al discuss the preparation of certain 4-aza-steroid derivatives which are stated to be steroidal 5α-reductase inhibitors.

In International Publication No. WO 91/12261, Panzeri et al. discuss the preparation of 17β-substituted-4-aza-5α-androstan-3-one derivatives.

In U.S. Pat. No. 4,396,615, Steroids 38: 121–140, 1981 and J. Steroid Biochem. 19: 1491–1502, 1983; Petrow et al discuss certain 6-methylene progesterone derivatives stated to be inhibitors of steroid 5α-reductase.

In U.S. Pat. No. 4,377,584 (see e.g., column 13), U.S. Pat. No. 4,220,775 and in EP Publication No. 414 490 and 414 491, Rasmusson et al. discuss certain 17β-substituted-4-aza-5α-androstanones (including acyl amino substitutions) as steroid-5α-reductase inhibitors.

In EP Publication No. 052799, Alig et al discuss the use of certain D-homosteroids as steroid 5α-reductase inhibitors.

In U.S. Pat. No. 4,191,759, Johnston and Arth discuss N-substituted-17β-carbamoyl-androst-4-en-3-ones as steroid 5α-reductase inhibitors.

In BE 855 992, Benson and Blohm discuss steroidal inhibitors of testosterone 5α-reductase, for treating skin disorders.

In CA 970 692, Voight and Hsia discuss compounds inhibiting 5α-reductase activity.

In FR I 465 544, Jolly and Warnant discuss 4-aza-aromatic steroid derivatives as steroid 5α-reductase inhibitors.

In U.S. Pat. No. 4,087,461, Robinson discuss certain allenic steroids as testosterone 5α-reductase inhibitors.

In EP Publication No. 414 529, Metcalf discuss certain 17-substituted steroidal acids as testosterone 5α-reductase inhibitors (see e.g. the Abstract). See Also, Holt, et al., EP Publication No. 427,434.

In EP Publication No. 298 652, Bhattacharya disclose the synthesis of 4-aza-Δ1-steroids.

In. U.S. Pat. No. 5,061,803 and 5,061,801, Williams discusses a method for the synthesis of 17β-alkanoyl3-oxo-4-aza-5α-androst-1-enes and 3-oxo-4-aza-androst-1-ene 17β-ketones.

In U.S. Pat. No. 5,061,802, Steinberg and Rasmusson discuss the preparation of 17β-aminobenzoyl-4-aza-5α-androst-1-en-3-ones as benign prostatic hypertrophy agents.

Lan-Hargest et al. discuss the synthesis of bridged A ring steroids as 5α-reductase inhibitors (Tetrahedron Lett. 28:6117–6120, 1987).

Weintraub et al (in J. Med. Chem. 28: 831–833, 1985) discuss the preparation of 20-hydroxymethyl-4-methyl-4-aza-2-oxa-5α-pregnan-3-one as inhibitors of testosterone 5α-reductase.

Kadohama et al. (Cancer Res. 44: 4947–4954, 1984) discuss sodium 4-methyl-3-oxo-4-aza-5α-pregnane-20 (S) carboxylate inhibition of prostatic tumor 5α-reductase.

MacIndoe et al. in Steroid Biochem. 20, 1095–1100, 1984, discuss the 5α-reductase inhibiting effect, in MCF-7 human breast cancer cells and rat prostate, of certain 6-methylene steroids.

Liang et al (J. Biol. Chem. 256:7998–8005, 1981) discuss 17β-N,N-diethylcarboxyamoyl-4-methyl-4-aza-5α-androstan-3-one as a reversible inhibitor of 5α-reductase.

Salomons and Doorenbos (J. Pharm. Sci. 63:19–23, 1974) and Doorenbos et al. (J. Pharm. Sci. 60:1234–1235, 1971; idem 62:638–640, 1973; Chem and Ind; 1322, 1970) discuss synthesis of 17β amino 4-aza- steroids.

Nakayama et al. (J. Antibiotics XLII:1221–1229, 1989; idem, 1230–1234, 1989; idem, 1235–1240, 1989) discuss the isolation of WS-9659 from Streptomyces and its inhibitory activity on testosterone 5α-reductase.

In EP Publication No. 294 937 and Publication No. 294 035, Nakai et al. discuss the preparation, respectively, of cinnamoyl amide derivatives and ((benzoylamino)phenoxy) butanoic acid derivatives, as inhibitors of 5α-reductase.

U.S. Pat. 5,026,882 and EP Publication No. 375 349 relates to certain steroid-3-phosphinic acid compounds for use as inhibitors of steroid 5α-reductase. These patents also summarize in their description of the related art, numerous compounds which are stated to be prior art 5α-reductase inhibitors. See, for example, Table I of U.S. Pat. No. 5,026,882 and the discussion in the prior art section of the patent.

EP Publication No. 435 321 relates to A-nor-steroid-3-carboxylic acid derivatives, which reportedly exhibit 5α-reductase inhibition.

In International Publication No. WO 91/13060 and EP Publication No. 458 207, Okada et al. discuss the preparation of Indole derivatives as testosterone 5α-reductase inhibitors.

Salle, et al., "17β-acylurea Derivatives of 4-Azasteroids as Inhibitors of Testosterone 5α-Reductase" relates to studies regarding the effectiveness on 5α-reductase of a new series of 17β-acylurea substituted derivatives.

U.S. Pat. No. 5,053,403 describes the use of certain androgen receptor blocking agents together with certain 5α-reductase enzyme inhibitor in the treatment or prevention of sebaceous gland hypertrophy, hirsutism and male-pattern baldness.

Prior art inhibitors of 5α-reductase are not believed to fully inhibit both forms of 5α-reductase without exhibiting or causing undesirable androgenic or other hormonal activity.

SUMMARY OF THE INVENTION

During treatment of certain diseases whose progress is stimulated by the activation of androgen receptors, it is desirable to reduce activation of those receptors. This may be accomplished by reducing the availability of "agonists", e.g., natural androgens and other compounds capable of activating the receptors or by reducing the availability of receptors and/or by blocking access to the receptors by compounds which would otherwise activate them. The latter function may be achieved by administering an "antagonist", a compound with affinity for a receptor which binds the receptor and blocks access by agonists. In the case of androgen receptors, an androgen antagonist ("an antiandrogen") may desirably bind the androgen receptor without activating the receptor. Its physical presence blocks access to the receptor by natural or other androgens which, given access to the receptor, could bind and activate the receptor.

In accordance with the present invention, novel testosterone 5α-reductase inhibitors are used in the treatment of androgen-sensitive diseases whose progress can be slowed by inhibiting activation of androgen receptors. Compounds of the invention inhibit the activity of 5α-reductase which catalyzes the synthesis of the potent androgen, dihydrotestosterone. Thus, availability of dihydrotestosterone to activate androgen receptors is desirably reduced.

It is important to achieve this desirable reduction of 5α-reductase activity without causing adverse effects on the ultimate goal of inhibiting activation of androgen receptors. Hence, even if a compound effectively inhibits 5α-reductase activity, its therapeutic effect is reduced if the inhibitor itself has inherent androgenic properties such that the inhibitor activates the very receptors whose activation it is intended to reduce. Likewise, the inhibitor should resist being converted in vivo into an androgenic compound.

Conversely, however, a 5α-reductase inhibitor having antiandrogenic properties, displays two, rather than one, desirable effect on the treatment of androgen-related diseases. First, it inhibits enzymatic conversion of testosterone to dihydrotestosterone, thus reducing the amount of dihydrotestosterone available to activate androgen receptors. Second, it antagonistically blocks androgen receptors. shielding them from activation by any available androgens, including any dihydrotestosterone which may have been synthesized in spite of the inhibitor.

Thus, inhibitors of 5α-reductase activity preferably display a combination of desirable qualifies, including (A) an ability to effectively inhibit 5α-reductase activity (preferably both types of 5α-reductase); and (B) a substantial lack of androgenic activity (and resistance to being converted in vivo into an androgen). It is also desirable that the inhibitors have antiandrogenic properties. In order to eliminate undesirable side effects, preferred 5α-reductase inhibitors also substantially lack glucocorticoid characteristics.

It is, accordingly, an object of the present invention to provide improved 5α-reductase inhibitors which more effectively inhibit 5α-reductase activity, and preferably inhibit the activity of both known types of human 5α-reductase.

It is another object of the invention to provide pharmaceutical compositions having 5α-reductase inhibitors possessing little intrinsic androgenic activity and little propensity to be converted in vivo to another compound possessing intrinsic androgenic activity.

It is another object of the invention to provide methods for the treatment of androgen-related diseases whose progress is aided by activation of androgen receptors. Such diseases include, for example, prostate cancer, prostatic hyperplasia and sexual deviance and may be treated by the methods of reducing 5α-reductase activity provide herein.

Methods of treatment are provided which utilize 5α-reductase inhibitors of the invention, either alone or in combination with another active ingredient, e.g., an antiandrogen, as part of a combination therapy.

The foregoing and other objects may be achieved by providing pharmaceutical compositions comprising the 5α-reductase inhibitors disclosed herein together with pharmaceutically acceptable carriers or diluents. These pharmaceutical compositions are administered to a patient afflicted with a disease such as those discussed above, whose progress is aided by activation of androgen receptors.

In one embodiment of the invention, a pharmaceutical composition is provided which comprises a pharmaceutically acceptable diluent or carrier and a testosterone 5α-reductase having the molecular formula:

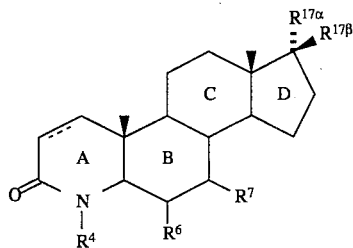

wherein the dotted line is an optional pi bond;

wherein $R^4$ is hydrogen or methyl;

wherein $R^6$ is hydrogen or $C_1$–$C_3$ saturated or unsaturated hydrocarbon;

wherein $R^7$ is selected from the group consisting of hydrogen, $C_1$–$C_6$ alkyl, $C_1$–$C_6$ hydroxyalkyl, $C_1$–$C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing;

wherein $R^{17\alpha}$ is hydrogen or lower alkyl; and wherein $R^{17\beta}$ is a tertiary amino or amido group.

In another embodiment of the invention, a pharmaceutical composition is provided which comprises a pharmaceutically acceptable diluent or carrier and a therapeutically effective amount of an inhibitor of testosterone 5α-reductase having the molecular formula:

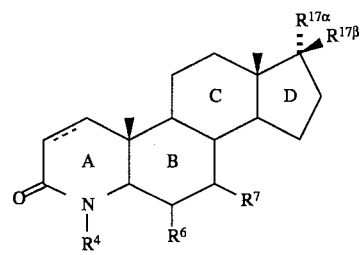

wherein the dotted line is an optional pi bond;

wherein $R^4$ is hydrogen or methyl;

wherein $R^6$ is hydrogen or $C_1$–$C_3$ saturated or unsaturated hydrocarbon;

wherein $R^7$ is selected from the group consisting of hydrogen, $C_1$–$C_6$ alkyl, $C_1$–$C_6$ hydroxyalkyl, $C_1$–$C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing;

wherein $R^{17\beta}$ is selected from the group consisting of a $C_1$–$C_6$ alkyl, $C_1$–$C_6$ hydroxyalkyl, $C_1$–$C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing; and wherein $R^7$ is hydrogen, hydroxy or a substituent converted in vivo to hydroxy.

In another embodiment of the invention, a pharmaceutical composition is provided comprising a pharmaceutically acceptable diluent or carrier and a therapeutically effective amount of an inhibitor of testosterone 5α-reductase having the molecular formula:

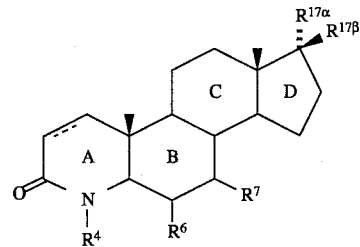

wherein the dotted line is an optional pi bond;

wherein $R^4$ is hydrogen or methyl;

wherein $R^6$ is $C_1$–$C_3$ saturated or unsaturated hydrocarbon;

wherein $R^7$ is selected from the group consisting of hydrogen, $C_1$–$C_6$ alkyl, $C_1$–$C_6$ hydroxyalky, $C_1$–$C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing;

wherein $R^{17\alpha}$ is hydrogen or lower alkyl; and wherein $R^{17\beta}$ is selected from the group consisting of acyl, carboxamide, tertiary amino and tertiary amido.

In another embodiment, a pharmaceutical composition is provided comprising a pharmaceutically acceptable diluent or carrier and a therapeutically effective amount of an inhibitor of testosterone 5α-reductase having the molecular formula:

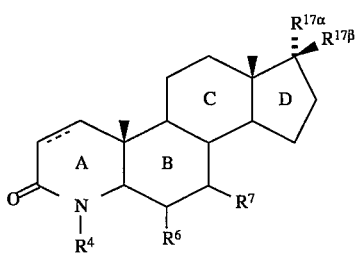

wherein the dotted line is an optional pi bond;
wherein $R^4$ is hydrogen or methyl;
wherein $R^6$ is hydrogen or $C_1$–$C_3$ saturated or unsaturated hydrocarbon;
wherein $R^7$ is selected from the group consisting of $C_2$–$C_6$ alkyl, $C_2$–$C_6$ hydroxyalkyl, $C_2$–$C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing;
wherein $R^{17\alpha}$ is hydrogen or lower alkyl; and
wherein $R^{17\beta}$ is selected from the group consisting of acyl, carboxamide, tertiary amino and tertiary amido.

In another embodiment, a pharmaceutical composition is provided for the inhibition of testosterone 5α-reductase activity which comprises a pharmaceutically acceptable diluent or carrier and a therapeutically effective amount of a 5α-reductase inhibitor of the formula:

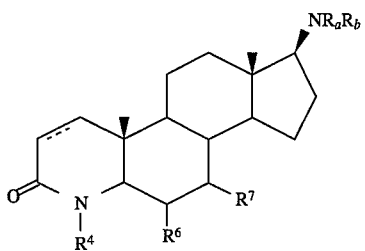

wherein the dotted line is an optional pi bond;
wherein $R^4$ is hydrogen or methyl;
wherein $R^6$ is hydrogen or $C_1$–$C_3$ saturated or unsaturated hydrocarbon;
wherein $R^7$ is selected from the group consisting of hydrogen, $C_1$–$C_6$ alkyl, $C_1$–$C_6$ hydroxyalkyl, $C_1$–$C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing;
wherein $R_a$ is selected from the group consisting of lower alkyl, cycloalkyl and a moiety which, together with $R_b$, and the nitrogen atom depicted at $R^{17\beta}$, is a 5–7 membered heterocyclic ring having a single nitrogen hetero atom; and
wherein $R_b$ is selected from the group consisting of a moiety which, together with $R_a$ and the nitrogen atom depicted at $R^{17\beta}$, is a 5–7 membered heterocyclic ring having a single nitrogen hetero atom; —$COR_C$, —$CONR_CR_D$, —$CSNR_CR_D$, —$SO_2R_C$, —$PO_3R_CR_D$ ($R_C$ and $R_D$ being hydrogen, lower alkyl or lower haloalkyl).

Capsules having the 5α-reductase inhibitors discussed herein may also be utilized. The inhibitors and compositions containing them are utilized in accordance with the invention in methods for reducing 5α-reductase activity, and in the treatment of diseases when progress is aided by activation of androgen receptors, e.g. prostate cancer, benign prostatic hyperplasia, acne, seborrhea, hirsutism, androgenic alopecia and the like.

DETAILED DESCRIPTION OF THE PREFERRED EMBODIMENTS

In some, but not all, embodiments, an azasteroidal nucleus has a substituent (i.e., other than hydrogen), on at least one of the 4, 6 or 7 positions, e.g., 4-methyl and/or 6-lower alkyl and/or 7-lower alkyl.

In some embodiments, the $R^{17\beta}$ substituent is a tertiary amine such as —$N(R^{19})(R^{20})$ where $R^{19}$ is lower alkyl or haloalkyl, and $R^{20}$ is lower alkyl. In other embodiments, $R^{17\beta}$ is a tertiary amido substituent, e.g., acylamino substituents such as —$N(R^{25})C(O)R^{26}$, wherein $R^{26}$ is hydrogen or a lower alkyl and $R^{25}$ is a $C_1$–$C_6$ saturated or unsaturated hydrocarbon such as cyclopropyl, cyclohexyl, butyl or isobutyl.

As used herein, the terms "tertiary amino" or "tertiary amido" refer to amino or amido substituents wherein the amino or amido nitrogen is not hydrogen substituted. Preferred substituents for the nitrogen include but are not limited to acyl and lower alkyl.

In order to avoid steric interaction between the $R^{17\alpha}$ and $R^{17\beta}$, it is preferred that at least one of these two substituents be hydrogen, hydroxy or a substituent which is converted to hydroxy in vivo (e.g., benzoyloxy, acetoxy).

Hydrocarbon substituents may be saturated or unsaturated. Unsaturated substituents are believed to be especially useful at the $R^7$ and $R^{17\beta}$ positions. In some embodiments, $R^7$ is a $C_2$–$C_6$ alkyl, alkenyl or alkynyl substituent.

In some embodiments, especially when $R^{17\beta}$ is hydrogen, hydroxyl (or an ester derivative thereof, $R^{17\alpha}$ is $C_1$–$C_6$ alkyl, $C_1$–$C_6$ hydroxyalkyl, $C_1$–$C_6$ haloalkyl, $C_2$–$C_6$ carbonylalkyl, $C_3$–$C_6$ epoxyalkyl or an unsaturated analog of the foregoing. Preferred unsaturated analogs include, for example, halo or hydroxy alkynyl or alkenyl substituents, especially where the halo or hydroxy group is at the end of the substituent, i.e., farthest from the aza-steroidal D-ring. An unsaturation at the 1, 2 or 3 position of the 17α substituent is also preferred.

Except where otherwise specified, substituents may have α or β stereochemistry. Optional pi bonds denoted by dotted lines in a molecular structure are independent of any other optional bonds appearing in that structure, the presence of one not being dependent on the presence or absence of another, unless valence requires interdependency. Compounds discussed herein may be formulated as salts thereof. Atoms of the azasteroidal nucleus for which no substituent is shown may optionally be further substituted (as valence permits) so long as such substitution does not adversely affect the compound's ability to inhibit 5α-reductase activity, and does not render the compound substantially more androgenic.

As used herein, the term "lower" when describing a chemical moiety means a moiety having 8 or fewer atoms. For instance, a "lower alkyl" means a $C_1$ to $C_8$ alkyl. Any moiety of more than two atoms may be straight- or branch-chained unless otherwise specified.

As discussed in more details below, carriers or diluents include solids and liquids. The novel pharmaceutical compositions of the invention may be used in the treatment of androgen-related diseases. When administered systemically by injection, e.g., for treatment of prostate cancer, benign prostatic hyperplasia, and other diseases not primarily effecting the skin, conventional diluents or carriers which are known in the art to be pharmaceutically acceptable for systemic use are used, e.g., saline, water, aqueous ethanol and oil. When the inhibitors of the invention are utilized for the treatment of androgen related diseases such as acne, seborrhea, hirsutism, androgenic alopecia, the inhibitors are preferably administered together with a conventional topical carrier or diluent such as a mixture of ethanol and propylene glycol. When used topically, it is preferred that the diluent or carrier does not promote transdermal penetration of the active ingredients into the blood stream or other tissues where they might cause unwanted systemic effects. When a composition is prepared other than for immediate use, an art recognized preservative is typically included (e.g. benzyl alcohol).

When the compound is administered in a cutaneous or topical carrier the carrier may be any known carrier in the cosmetic and medical arts, e.g. any gel, cream, lotion, ointment, liquid or non liquid carrier, emulsifier, solvent, liquid diluent or other similar vehicle which does not exert deleterious effect on the skin or other living animal tissue. Examples of suitable topical carriers include, but are not limited to liquid alcohols, liquid glycols, liquid polyalkylene glycols, water, liquid amides, liquid esters, liquid lanolin and lanolin derivatives and similar materials. Alcohols include mono and polyhydric alcohols, including ethanol, glycerol, sorbitol, isopropanol, diethylene glycol, propylene glycol, ethylene glycol, hexylene glycol, mannitol and methoxyethanol. Typical carriers may also include ethers, e.g. diethyl and dipropyl ether, methoxypolyoxyethylenes, carbowaxes, polyethyleneglycerols, polyoxyethylenes and sorbitols. Usually, the topical carrier includes both water and alcohol in order to maximize the hydrophylic and lipophylic solubility. A typical carrier will comprise 75% ethanol or isopropanol and 15% water.

The topical carrier may also include various ingredients commonly used in ointments and lotions and well known in the cosmetic and medical arts. For example, fragrances, antioxidants, perfumes, gelling agents, thickening agents such as carboxymethylcellulose, surfactants, stabilizers, emollients, coloring agents and other similar agents may be present.

As illustrated by the examples which follow, the compositions of the present invention may contain well-known and currently used ingredients to form creams, lotions, gels and ointments which are dermatologically acceptable and non toxic. The composition may be applied as a gel, a cream, an ointment, a lotion or the like.

A dry delivery system, as described in U.S. Pat. Nos 3,742,951, 3,797,494 or 4,568,343 may be used.

Solvents or devices as described in U.S. Pat. Nos 5,064,654, 5,071,644 or 5,071,657 can also be used to facilitate transdermal penetration when systemic effects are desired.

The compound can also be administered by the oral route. The compound in the present invention can be typically formulated with conventional pharmaceutical excipients, e.g. spray dried lactose and magnesium stearate into tablets or capsules for oral administration. Of course, taste-improving substances can be added in the case of oral administration forms. When capsules for oral ingestion are desired, any pharmaceutical capsules known in the art may be filled with the 5α-reductase inhibitors of the invention, with or without additional diluents and other additives discussed herein.

The active substance can be worked into tablets or dragee cores by being mixed with solid, pulverulent carrier substances, such as sodium citrate, calcium carbonate or dicalcium phosphate, and binders such as polyvinyl pyrrolidone, gelatin or cellulose derivatives, possibly by adding also lubricants such as magnesium stearate, sodium lauryl sulfate, "Carbowax" or polyethylene glycol.

As further forms, one can use plug capsules, e.g. of hard gelatin, as well as closed solf-gelatin capsules comprising a softner or plasticizer, e.g. glycerine. The plug capsules contain the active substance preferably in the form of granulate, e.g. in mixture with fillers, such as lactose, saccharose, mannitol, starches, such as potato starch or amylopectin, cellulose derivatives or highly dispersed silicic acids. In solf-gelatin capsules, the active substance is preferably dissolved or suspended in suitable liquids, such as vegetable oils or liquid polyethylene glycols.

The following non-limiting examples describe the preparation of a typical cream, lotion, gel and ointment, respectively. In addition to these vehicles, one skilled in the art may choose other vehicles in order to adapt to specific dermatologic needs.

EXAMPLE A. A typical lotion contains (W/W) 5% active compound, 15% propylene glycol and 75% ethanol and water 5%.

EXAMPLE B. A typical gel contains (W/W) 5% active compound, 5% propylene glycol, 0.2% Carbomer 940 (available as Carbopol 940$^R$ from B. F. Goodrich), 40% water, 0.2% triethanolamine, 2% PPG-12-Buteh-16 (available as Ucon$^R$ fluid 50 from Union Carbide), 1% hydroxypropyl and 46.8% ethanol (95% ethanol-5% water).

EXAMPLE C. A typical ointment contains (W/W) 5% active compound, 13% propylene glycol, 79% petrolatum, 2.9% glycerylmonostearate and 0.1% polylparaben.

EXAMPLE D. A typical cream contains (W/W) 5% active compound, 0.2% propylparaben, 5% lanolin oil, 7.5% sesame oil, 5% cetyl alcohol, 2% glyceryl monostearate, 1% triethanolamine, 5% propylene glycol, 0.1% Carbomer 940$^R$ and 69.2% water.

The 5α-reductase inhibitors of the invention are preferably formulated into pharmaceutical compositions at conventional concentrations for 5α-reductase inhibitors. The attending clinician may elect to modify the concentration and/or dosage in order to adjust the dose to the particular response of each patient.

When 5α-reductase activity inhibitors are administered in accordance with the invention, they are preferably administered orally or parenterally. Dosage preferably ranges from about 1 mg to about 1000 mg of active expedient, i.e., 5α-reductase inhibitor(s), per day per 50 kg of body weight, most preferably from about 2.5 mg to about 500 mg per day per 50 kg of body weight.

Concentration of active expedient varies in a known manner depending upon the method of administering the pharmaceutical composition. A composition suitable for oral administration may preferably include at least one inhibitor of 5α-reductase activity wherein the total concentration of all such inhibitors in said pharmaceutical composition is from about 1% to 95% of the composition (by weight), and preferably from about 5% to about 20%. The pharmaceutically acceptable diluent is preferably starch or lactose (with or without tartrazine).

When prepared for parental injection, the inhibitor is preferably added at a concentration between about 2.0 mg/ml and about 50 mg/ml (preferably about 5.0 mg/ml to about 20 mg/ml) into a carrier preferably selected from the group consisting of saline, water, aqueous ethanol and oil.

In certain alternative embodiments, the pharmaceutical composition of the invention may be formulated for sustained release in accordance with known techniques. The sustained release formulations are preferably prepared in a known manner appropriate for either oral, intramuscular or subcutaneous administration.

When the pharmaceutical composition is for topical use, the 5α-reductase inhibitor(s) is preferably formulated together with a carrier selected from the group consisting of propylene glycol, ethanol, isopropanol and water at a concentration ranging from 0.5% to 10% by total weight of the pharmaceutical composition. The composition for topical use may be formulated, for example, as an ointment, a gel, a cream or a lotion, to be applied to affected areas of the skin in need of treatment twice daily.

In some embodiments of the invention, the 5α-reductase inhibitors of the invention are used in combination with another active ingredient as part of a combination therapy. For example, the novel inhibitors may be utilized together with a separate antiandrogen which may be incorporated into the same pharmaceutical composition as the 5α-reductase inhibitor, or which may be separately administered. An active compound may possess both antiandrogenic and 5α-reductase inhibiting activity, and may be supplemented with another compound to reinforce either or both of these activities (e.g., another antiandrogen or another inhibitor of 5α-reductase). Combination therapy could also include treatment with one or more compounds which inhibit the production of testosterone or its precursors.

When antiandrogen is used in a combination therapy in addition to the 5α-reductase inhibitors of the invention, the antiandrogen may be, for example:

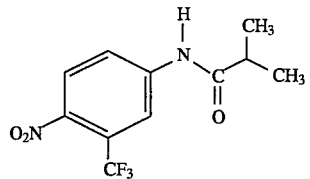

Flutamide (systemic)

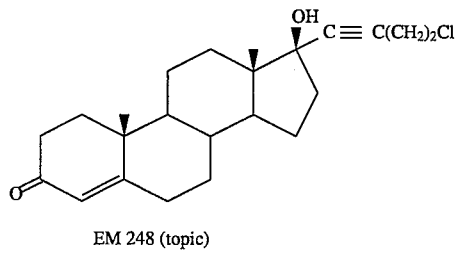

EM 248 (topic)

The antiandrogen is formulated at conventional concentrations and administered at conventional dosages, e.g., at the same concentrations and dosages set forth above for the 5α-reductase inhibitor.

The antiandrogen Flutamide is commercially available from Schering Corp. (New Jersey). The antiandrogen EM-248 may be synthesized as follows:

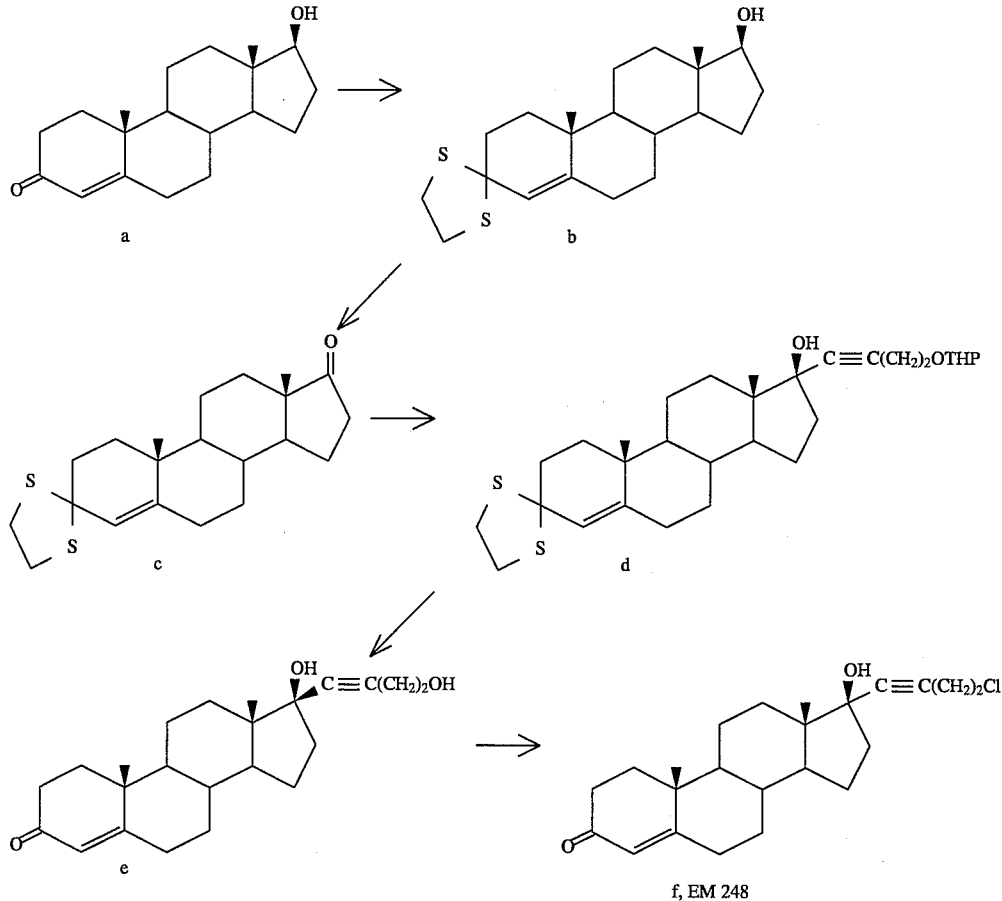

Compound b

To a solution of testosterone 1 (288.43 g, 1.0 mole) in glacial acetic acid (3.5 L), ethanedithiol (85 ml, 1.01 mole) and boron trifluoride (800 ml) were added at 10° C. The mixture was stirred at this temperature for 1 hour and poured over ice (2 kg). From this aqueous phase a white solid separated and was collected by filtration, washed with water (2×2 L) and air dried. Crystallization from methanol gave the pure compound b. Yield: 328.28 g (90%).

Compound c

A solution of b (182.3 g, 0.5 mole) in dry dichloromethane (1.5 L) was added dropwise to a solution of pyridinium chlorochromate (150 g, 0.7 mole), molecular sieves 3A (200 g) and sodium acetate (25 g) at room temperature with mechanical stirring. After the addition was completed, the mixture was stirred for 16 hours and then diluted with diethyl ether (2 L) and filtered through silica gel in a fritted funnel. The filtrate was concentrated in vacuo and the resulting solid was crytallized from methanol to give the pure compound c. Yield: 158.7 g, (87%).

Compound d 2-(3- Butynyloxy)tetrahydro-2H-pyran (112.5 g, 0.729 mole) was added dropwise to a solution of methyllithium (500 ml of MeLi 1.4M in ether, .70 mole) in 1 L of anhydrous THF at −30° C. under argon atmosphere in a 5 L round bottom flask. After the addition was completed, the cooling bath was removed and the solution was allowed to stand at room temperature for 4 hours. The solution was cooled again at −30° C. and a solution of c (75 g, .207 mole) in 2.5 L of anhydrous THF was added dropwise. After the addition, the cooling bath was removed and the mixture was allowed to stand at room temperature for 16 hours. To this mixture, 100 ml of brine was added and the solution was diluted with ethyl acetate washed with brine and dried with anhydrous MgSO$_4$. The solvent was evaporated and a solid crystallized after a short period of time. Hexane was added to complete the precipitation. The solid was then filtered and washed with hexane. The compound was used in the next step without further purification. Yield: 95.8 g ( 90%).

Compound e

A mixture of compound d (30 g, .058 mole) and methyliodide (65 ml, 1 mole) in methanol 96% (750 ml) was heated under reflux for 16 hours. The solvent was then removed in vacuo and the crude mixture was diluted with ethyl acetate (1 L). The organic phase was washed with NaOH 3% (3× 500 ml) and dried over MgSO$_4$. After the evaporation of the solvent the solid was washed with diethyl ether, filtered on a fritted funnel and washed again with diethyl ether. This compound can be used without further purification in the last step. Yield 65%.

17α-(chlorobutynyl)-17β-hydroxy 4-androsten-3-one (f, EM 248)

A mixture of compound d (15 g, .04 mole), triphenylphosphine (21 g, .08 mole) and carbon tetrachloride (9.3, .06 mole) was heated under reflux in 1 L of anhydrous dichloromethane for 10 hours. After the evaporation of the solvent the crude mixture was adsorbed on silica gel and chromatographied on silica gel (flash) with diethyl ether:hexane (70:30). The compound was further purified by crystallization in diethyl ether. Yield 85%.

A combination therapy involving 5α-reductase inhibitor and antiandrogen has the beneficial effect of inhibiting activation of androgen receptors by two different mechanisms without significantly reducing testosterone levels, the reduction of which may cause undesirable side effects in some patients. In appropriate cases, i.e. where prostate cancer or another androgen related disease is not responding acceptably to treatment, a concurrent therapy designed to decrease testosterone levels may also be utilized (e.g., surgical or chemical castration, for example, by administering a LHRH agonists or antagonists known in the art).

Inhibitors of testosterone 5α-reductase of the formula:

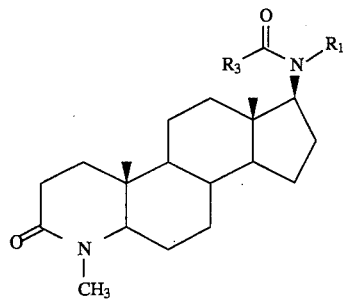

include but are not limited to those set forth in Table I below:

TABLE I

| Inhibitor | R$_1$ | R$_3$ | 5α-reductase inhibition Ki (nM) |
|---|---|---|---|
| EM 316 | CH$_3$ | H | 29 |
| EM 336 | Cyclo C$_3$H$_5$ | H | 11.2 |
| EM 337 | Cyclo C$_6$H$_{11}$ | H | 11.9 |
| EM 347 | C$_4$H$_9$ | H | 2.6 |
| EM 401 | C$_5$H$_{11}$ | H | 1.8 |
| EM 402 | C$_6$H$_{13}$ | H | 7.2 |
| EM 405 | Iso amyl | H | 2.2 |
| EM 407 | Ethylpropyl | H | 10.6 |
| EM 422 | Iso C$_4$H$_9$ | H | 7.3 |
| EM 423 | C$_3$H$_7$ | H | 5.1 |
| EM 424 | C$_4$H$_9$ | CH$_3$ | 11.8 |
| EM 436 | CH$_2$C$_6$H$_5$ | H | 5.6 |

Testosterone 5α-reductase inhibitors of the formula:

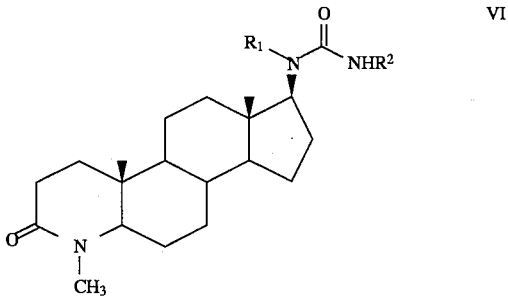

include but are not limited to those set forth in Table II below:

TABLE II

| Compound | R$_1$ | R$_2$ | 5α-reductase inhibition Ki (nM) |
|---|---|---|---|
| EM 373 | Cyclo C$_3$H$_5$ | CH$_3$ | 0.5 |
| EM 374 | Cyclo C$_3$H$_5$ | C$_6$H$_5$ | 2.3 |
| EM 390 | Cyclo C$_3$H$_5$ | C$_3$H$_7$ | 7.1 |
| EM 392 | Cyclo C$_3$H$_5$ | C$_2$H$_5$ | 13.5 |
| EM 394 | Cyclo C$_3$H$_5$ | C$_4$H$_9$ | 3.3 |
| EM 396 | Cyclo C$_3$H$_5$ | IsoC$_3$H$_7$ | 14.0 |
| EM 397 | Cyclo C$_3$H$_5$ | Cyclo C$_6$H$_{11}$ | 3.2 |
| EM 408 | CH$_3$ | C$_6$H$_5$ | 8.2 |

Testosterone 5α-reductase inhibitors of the formula:

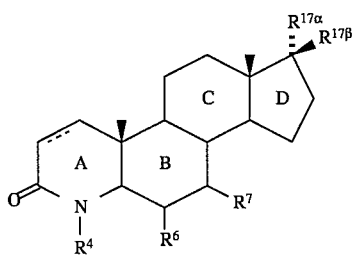

include but are not limited to those set forth in Tables I and II as well as those compounds set forth below in Table III.

TABLE III

| Compound | Steroid nucleus | $R^4$ | $R^6$ | $R^7$ | $R^{17\alpha}$ | $R^{17\beta}$ |
|---|---|---|---|---|---|---|
| EM 316 | Nil | $CH_3$ | H | H | H | $N(CH_3)CHO$ |
| EM 336 | Nil | $CH_3$ | H | H | H | $N(C_3H_5)CHO$ |
| EM 337 | Nil | $CH_3$ | H | H | H | $N(C_6H_{11})CHO$ |
| EM 347 | Nil | $CH_3$ | H | H | H | $N(C_4H_9)CHO$ |
| EM 401 | Nil | $CH_3$ | H | H | H | $N(C_5H_{11})CHO$ |
| EM 402 | Nil | $CH_3$ | H | H | H | $N(C_6H_{13})CHO$ |
| EM 405 | Nil | $CH_3$ | H | H | H | $N(iso\text{-}amyl)CHO$ |
| EM 407 | Nil | $CH_3$ | H | H | H | $N(ethylpropyl)CHO$ |
| EM 422 | Nil | $CH_3$ | H | H | H | $N(iso\text{-}C_4H_9)CHO$ |
| EM 423 | Nil | $CH_3$ | H | H | H | $N(C_3H_7)CHO$ |
| EM 424 | Nil | $CH_3$ | H | H | H | $N(C_4H_9)COCH_3$ |
| EM 436 | Nil | $CH_3$ | H | H | H | $N(CH_2C_6H_5)CHO$ |
| EM 373 | Nil | $CH_3$ | H | H | H | $N(Cyclo\text{-}C_3H_5)CONHCH_3$ |
| EM 374 | Nil | $CH_3$ | H | H | H | $N(Cyclo\text{-}C_3H_5)CONHC_6H_5$ |
| EM 390 | Nil | $CH_3$ | H | H | H | $N(Cyclo\text{-}C_3H_5)CONHC_3H_7$ |
| EM 392 | Nil | $CH_3$ | H | H | H | $N(Cyclo\text{-}C_3H_5)CONHC_2H_5$ |
| EM 394 | Nil | $CH_3$ | H | H | H | $N(Cyclo\text{-}C_3H_5)CONHC_4H_9$ |
| EM 396 | Nil | $CH_3$ | H | H | H | $N(Cyclo\text{-}C_3H_5)CONH(Iso\text{-}C_3H_7)$ |
| EM 397 | Nil | $CH_3$ | H | H | H | $N(Cyclo\text{-}C_3H_5)CONH(Cyclo\text{-}C_6H_{11})$ |
| EM 408 | Nil | $CH_3$ | H | H | H | $N(CH_3)CONHC_6H_5$ |
| EM 409 | Nil | $CH_3$ | H | H | H | $N(CH_3)CONHCH_3$ |
| EM 322 | Nil | $CH_3$ | H | H | $C_3H_5$ | OH |
| EM 441 | Nil | H | H | H | $C_3H_5$ | OH |
| EM 378 | Nil | $CH_3$ | H | H | $C_3H_7$ | OH |
| EM 352 | Nil | H | H | H | $C_3H_7$ | OH |
| EM 450 | Nil | $CH_3$ | H | H | H | $N(C_4H_9)COCH_2Cl$ |
| EM 314 | $\Delta^1$ | $CH_3$ | H | H | H | $N(CH_3)CHO$ |
| EM 420 | $\Delta^1$ | $CH_3$ | H | H | H | $N(Cyclo\text{-}C_3H_5)CONHC_2H_5$ |
| EM 346 | $\Delta^1$ | H | H | H | H | $N(CH_3)CHO$ |
| EM 448 | Nil | H | H | H | $C \equiv C(CH_2)_2I$ | OH |
| EM 465 | Nil | H | H | H | $C \equiv C(CH_2)Br$ | OH |
| EM 358 | Nil | H | H | H | $C \equiv C(CH_2)_3Br$ | OH |
| EM 471 | Nil | H | H | H | $C \equiv C(CH_2)_3I$ | OH |
| EM 321 | Nil | $CH_3$ | H | H | $C \equiv C(CH_2)_2Br$ | OH |
| EM 320 | Nil | $CH_3$ | H | H | $C \equiv C(CH_2)_2I$ | OH |
| EM 501 | Nil | H | H | H | $C \equiv C(CH_2)_2Cl$ | OH |
| EM 502 | Nil | $CH_3$ | H | H | $C \equiv C(CH_2)_2Cl$ | $OCOC_6H_5$ |
| EM 503 | Nil | $CH_3$ | H | H | $C \equiv C(CH_2)_2Cl$ | OH |
| EM 548 | Nil | $CH_3$ | $CH_3$ | H | H | $N(C_4H_9)CHO$ |
| EM 561 | Nil | $CH_3$ | H | $C_4H_8OH$ | H | $N(C_4H_9)CHO$ |
| EM 572 | Nil | H | H | H | H | $N(C_4H_9)COCH_3$ |
| EM 591 | Nil | $CH_3$ | H | H | H | $N(C_4H_9)SO_2CH_3$ |
| EM 621 | Nil | $CH_3$ | H | H | H | $N(C_4H_9)PO_3(CH_3)_2$ |
| EM 435 | Nil | $CH_3$ | H | H | H | $N(ter\text{-}C_6H_{13})CHO$ |

Except where otherwise indicated, 5α-reductase inhibition is measured by the following method. Plates having 24 dishes per unit are used. Into each dish were placed 100,000 cells from the human carcinoma metastatic prostatic cell line DU 145 (ATCC #HTB 81) in MEM medium containing 2% dextran charcoal-treated calf serum, 1% penicillin, 1% streptomycin and 1% non essential amino acids. After 24 h, the medium was removed and replaced by 2.5 ml of MEM medium containing 2% dextran charcoal-treated calf serum, 10 nM of tritiated 4-androsten- 3,20-dione and 1% of ethanol. Each dish had different concentrations of the 5α-reductase inhibitor being tested. The cells were incubated for 24 h at 37° C. under an atmosphere of 5% $CO_2$ saturated with water. The extracellular medium was then removed, centrifuged at 1000 RPM for 10 min., and decanted in test tubes. To these test tubes was added 100 μl of ethanol containing 25 μg of androstanedione, 25 μg of 4-androstenedione, 25 μg of dihydrotestosterone and 25 μg of testosterone. The steroids were then extracted from the mixture by two extractions with 2 ml of diethyl ether. Phase separation was achieved by freezing of the aqueous phase. The organic phase was then evaporated, thus leaving asteroid residue which was dissolved in a few drops of methylene chloride and spotted on TLC plates (Whatman WH 4420222). After developing twice with a mixture of benzene-acetone (9:1), the spots were visualized by U.V. and gaseous iodine, cut, put into separate vials for each steroid and extracted for 15 min with 1 ml of ethanol. After addition of 10 ml of scintillation cocktail (NEN 989), the vials were shaked and counted.

The 5α-reductase activity is the sum of the transformation of 4-androstenedione to androstanedione and of the transformation of testosterone to dihydrotestosterone. Conversion of tritiated 4-androsten- 3,20-dione to other steroids in the presence of different concentrations of inhibitor and a constant concentration of radioactive 4-androstenedione is measured, and $IC_{50}$ (i.e. the concentration of inhibitor required to inhibit 50% of 5α-reductase activity) values are then used to calculate Ki values of inhibition for each compound according to Cheng and Prusoff (Biochem. Pharmacol. 22, 3099–3108, 1973).

Set forth below are non-limiting examples of methods of synthesizing 5α-reductase inhibitors for use in the present invention. Those of skill in the art may readily alter these syntheses by known conventional techniques to produce other 5α-reductase inhibitors of the invention.

EXAMPLES OF SYNTHESIS OF PREFERRED INHIBITORS OF STEROID 5α-REDUCTASE ACTIVITY

EXAMPLE 1

Preparation of 17β-(N-n-butyl-N-formamido)-4-methyl-4-aza5α- androstan-3-one (11, $R_1=C_4H_9$, EM 347)

Synthesis described in scheme 1

Preparation of 17β-hydroxy-5-oxo-A-nor-3,5-secoandrostan-3-oic Acid (1). To a stirred mixture of the testosterone acetate (Steraloids Inc. Wilton N.H. USA) (200 g, 0.605 mol) in tert-butyl alcohol (2 L) was added a solution of sodium carbonate (96.3 g, 0.908 mol) in 460 mL of water. The mixture was brought to reflux and a solution of sodium periodate (893.8 g, 4.176 mol) and potassium permanganate (70.8 g, 0.448 mol) in warm water (75° C.) was added gradually (1 h) while the reflux temperature was maintained. The reaction was cooled to 30° C., and after 15 min the solids were removed by filtration. The solid was washed with 800 mL of water, and the combined filtrates were concentrated under reduced pressure to remove most of tert-butyl alcohol (final volume 1.0 L). The aqueous residue was cooled and acidified to pH 3.0 with concentrated hydrogen chloride solution. The aqueous solution was extracted with methylene chloride (4×800 mL) and the combined organic phase was washed with water, dried and concentrated to solid. Thus the solid obtained was subjected to acetate hydrolysis by refluxing with NaOH (34.3 g, 0.857 mol) in methanol (2.0 L) for 12 h. The reaction mixture was concentrated to 400 mL, diluted with water (600 mL) and acidified to pH 3. The solid was filtered, washed with water and dried. The filtrate was extracted with methylene chloride (3×1.0 L), and the combined organic phases were concentrated to syrup. Both the precipitates and the syrup were swished with boiling EtOAc and cooled at 0° C. for overnight to give 125 g (67% yield) of colorless crystals; mp 205°–207° C.

Preparation of 17β-hydroxy-4-methyl-4-aza-androst-5-ene-3-one (3). In a Schlenk tube, $MeNH_2$ was bubbled till saturation to a mixture of the seco acid 1 (8.0 g, 25.974 mmol) in ethylene glycol (80 mL) at room temperature. The clear yellowish solution was heated gradually (3° C./min) up to 180° C. and held at this temperature for 1 h. The reaction mixture was cooled to 10° C. and water (80 mL) was added with stirring. The solid was filtered, washed with water (20 mL) and dried to give 6.1 g of 3 (81%); mp 181°–183° C.

Preparation of 17β-hydroxy-4-methyl-4-aza-5α-androstan-3-one (5). A solution of the compound 3 (6 g, 20.7 mmol) in acetic acid (99.9%, 130 mL) was hydrogenated in the presence of platinium oxide (600 mg) at 45 p.s.i., starting at room temperature and heated to 60° C. over 12 h. The reaction mixture was cooled and filtered. The catalyst was washed with acetic acid (30 mL), and the combined filtrates were concentrated to a solid (5.5 g, 91%); mp 178°–180° C.

4-Methyl-4-aza-5αandrostan-3, 17-dione (7). The following method is the representative. To a stirred solution of compound 5 (7.3 g, 25 mmol) in methylene chloride (260 mL) was added pyridinium chlorochromate (8.1 g, 37 mmol) and the mixture was stirred at room temperature for 3 h. The contents were passed through Florisil (30–60 mesh) to remove the precipitates and the filtrates were washed with water (2×200 mL) and dried. The resulting residue was purified by flash column chromatography to give the dione 7 (4.4 g, 61%); mp 126°–128° C.

Preparation of 17β-(N-butyl)-amino-4-methyl-4-aza-5α-androstan-3-one (9, $R_1=C_4H_9$). The following method is representative. To a mixture of dione 7 (0.150 g, 0.495 mmol) and n-butylamine (0.040 g, 0. 54 mmol) in 1,2-dichloroethane was added sodium triacetoxyborohydride (0.156 g, 0.74 mmol) followed by acetic acid (0.03 g, 0.49 mmol) under argon at room temperature. After 16 h, the reaction mixture was diluted with methylene chloride (15 mL) and washed with 1N aqueous sodium hydroxide (2×20 mL), followed by brine (20 mL), dried and solvent removed to give the crude product which was purified by flash column chromatography to provide the 17-N-butyl-derivative (0.110 g, 61% yield).

Preparation of 17β-(N-n-butyl-N-formamido)-4-methyl-4-aza-5α-androstan-3-one (11, $R_1=C_4H_9$, EM 347). To a solution of formic acid (0.026 g, 0.556 mmol) in chloroform (1.5 mL) was added dropwise dicyclohexylcarbodiimide (DCC) (0.114 g, 0.56 mmol) in chloroform (1.5 mL) at 0° C. After 5 min the above solution was added to the compound 9 (0.10 g, 0.28 mmol) in pyridine (2 mL). The mixture was then stirred for 1 hours at room temperature. Evaporation of solvent was followed by addition of ether gave dicyclohexylurea which was removed via filtration and the solid was washed with ether. The combined filtrate was concentrated and purified by flash column chromatography to give the product 11, (EM 347) (0.075 g, 70%); $^1H$ NMR (CDCl$_3$): δ 0.66 (s,3H), 0.74–1.42 (m, 11H), 1.2–2.08 (m, 19H), 2.37–2.48 (m, 2H), 2.87 (s, 3H), 3.04 (dd, 1H, J=4, 13 Hz), 3.2–3.4 (m, 3H),8.12 (s, 0.8H), 8.24 (s, 0.2H); $^{13}C$ NMR (CDCl$_3$) δ 170.56, 164.54, 162.97, 68.59, 65.62, 51.99, 51.71, 44.11 ,36.85, 36.40, 34.12, 32.88, 30.64, 29.68, 29.04, 28.96, 25.20, 24.37, 22.86, 20.55, 20.21, 13.77, 12.34:. HRMS: calcd for $C_{24}H_{40}N_2O_2$, 388.3089; found 388.3147.

SCHEME 1

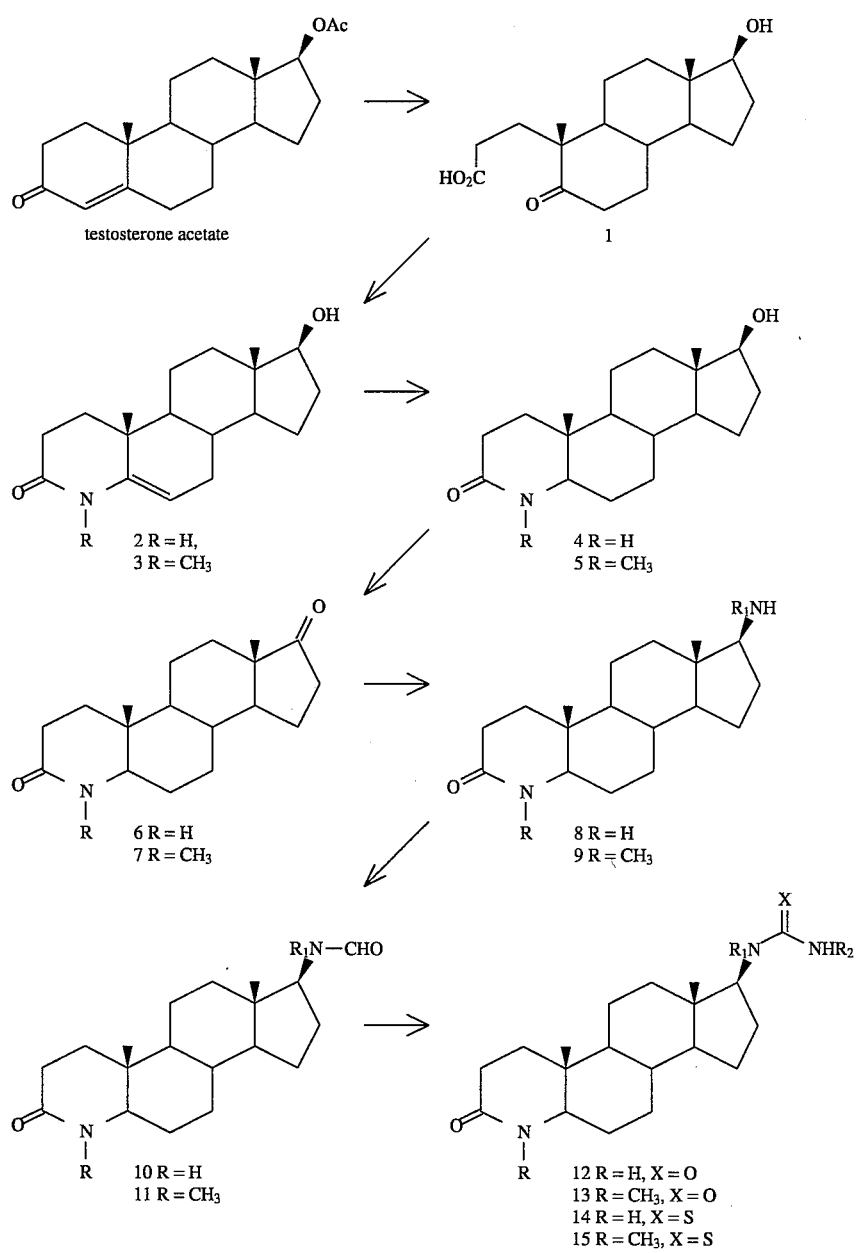

EXAMPLE 2

17β-(N-n-Amyl-N-formamido)-4-methyl-4-aza-5α androstan-3-one (11, $R_1=C_5H_{11}$, EM 401)

This synthesis is described in scheme 1

Preparation of 17β-(N-n amyl)-amino-4-methyl-4-aza-5α-androstan-3-one (9, $R_1=C_5H_{11}$). To a mixture of dione 7 (3.4 g, 22.6 mmol) and n-pentylamine (1.07 g, 12.3 mmol) in 1,2-dichloroethane was added sodium triacetoxyborohydride (3.5 g, 16.7 mmol) followed by acetic acid (0.68 g, 11.2 mmol) under argon at room temperature. After 16 h, the reaction mixture was diluted with methylene chloride (150 mL) and washed with 1N aqueous sodium hydroxide (2×200 mL), followed by brine (200 mL), dried and solvent removed to give the crude product which was purified by flash column chromatography to provide the 17-N-n-amyl-derivative (2.5 g, 61% yield).

Preparation of 17β(N-n-Amyl-N-formamido)-4-methyl-4-aza-5α-androstan-3-one (11, $R_1=C_5H_{11}$, EM 401). To a solution of formic acid (0.504 mL, 13.36 mmol) in chloroform (37 mL) was added dropwise dicyclohexylcarbodiimide (DCC) (2.75 g, 13.36 mmol) in chloroform (37 mL) at 0° C. After 5 min., the above solution was added to the compound 9 (2.5 g, 6.68 mmol) in pyridine (20 mL). The mixture was then stirred for 1 hours at room temperature. Evaporation of solvent was followed by addition of ether gave dicyclohexylurea which was removed via filtration and the solid was washed with ether. The combined filtrate was concentrated and purified by flash column chromatography to give the compound 11, $R_1=C_5H_{11}$ (EM-401) (2.5 g, 93%) The NMR spectroscopy analysis gave a (4:1) mixture of two conformers, M.P. 149°–151° C.; $^1$H NMR (CDCl$_3$):

δ 0.67 (s ,3H), 0.86 (s, 3H), 0.82–1.19 (m, 6H), 1.21–1.42 (m, 11H), 1.56–1.57 (m, 2H), 1.69–1.91 (m, 4H), 1.92–1.97 (m, 3H), 2.38–2.43 (m, 2H), 2.89 (s, 3H ), 3.0 (dd, 1H, J=3.2, 12.4 Hz), 3.21–3.28 (m, 3H), 8.14 (s, 0.8H), 8.2 (s, 0.2H); $^{13}$C NMR (CDCl$_3$):δ 170 .56, 164.8, 162.97, 68.54, 65.58, 61.98, 51.93, 51.66, 51.24, 46.69, 44.28, 37.24, 36.8, 36.37, 34.07, 32.83, 32.12, 29.64, 29.13, 29.04, 28.8, 28.19, 25.15, 24.33, 23.22, 22.84, 22.36, 20.51, 13.94, 12.75, 12.32;HRMS: calcd for C$_{25}$H$_{42}$O$_2$N$_2$, 402.3245, found 402.3242.

EXAMPLE 3

By analogous methods to those described in example 1, the following compounds were synthesized.

EM 316: 17β-(N-methyl-N-formamido)-4-methyl-4-aza-5α-androstan-3-one (11, R$_1$=CH$_3$). The product was prepared in 78% yield and the NMR spectroscopy analysis gave a mixture of two conformers, M.P. 194–196° C.; $^1$H NMR (CDCl$_3$): δ 0.74 (s, 2.4H), 0.75 (s, 0.6H), 0.88 (s, 0.6H),0.89 (s,2.4H), 0.78–1.14 (m, 3H), 1.26–1.47 (m, 6H ), 1.60–1.90 (m, 7H), 2.01–2.07 (m, 2H), 2.41–2.46 (m, 2H), 2.90 (s, 3H), 2.92 (s, 3H), 3.02–3.07 (dd, 1H, J=12.58, 3.2 Hz), 3.32 (t, 0.8H, J=9.6 Hz), 4.21 (t, 0.2H, J=10 Hz), 8.15 (s,0.8H), 8.18 (s, 0.2H); $^{13}$C NMR (CDCl$_3$): δ 170.45, 164.20, 163.32, 68.95, 65.43, 61.36, 51.82, 51.37, 51.12, 45.50, 44.21, 37.10, 36.66, 36.26, 33.87, 33.58, 32.70, 29.59, 29.51, 28.92, 28.83, 25.04, 23.03, 22.84, 22.74, 21.49, 20.35, 13.20, 12.61, 12.21;HRMS: calcd for C$_{21}$H$_{34}$N$_2$O$_2$, 346.2620; found, 346.2645.

EM 336: 17β-(N-Cyclopropyl-N-formamido)-4-methyl-4-aza-5α-androstan-3-one (11, R$_1$=cyclo C$_3$H$_5$). The product was prepared in 74% yield and the NMR spectroscopy analysis gave a mixture of two conformers, M.P. 163–165 ° C.; $^1$H NMR (CDCl$_3$): δ 0.39–0.44 (m, 0.4H), 0.61–0.85 (m, 10H), 0.86–1.17 (m, 2H), 1.18–1.41 (m, 7H), 1.42–1.56 (m, 1H), 1.57–2.06 (m, 6H), 2.35 (dd,J=4.5, 9.4 Hz, 2H), 2.38–2.54 (m, 2H), 2.85 (s, 3H), 2.97 (dd,J=3.4, 12.5 Hz, 1H), 3.24 (t,J=8.7, 8.9 Hz, 0.4H), 4.0 (t,J=9.2, 9.5 Hz, 0.6H),8.27(s,0.4H),8.33 (s,0.6H).$^{13}$C NMR (CDCl$_3$): δ 170.6, 165.4, 163.5, 69.9, 65.6, 64.4, 51.9, 51.8, 51.3, 45.7, 44.2, 37.9, 37.5, 36.4, 34.2, 29.7, 29.3, 29.1, 29.0, 28.8, 25.3, 22.2, 20.7, 13.6, 12.3, 9.9, 8.1, 6.4, 6.2.HRMS: calcd for C$_{23}$H$_{36}$N$_2$O$_2$, 372.2796; found 372.2820.

EM 337: 17β-(N-Cyclohexyl-N-formamido)-4-methyl-4-aza-5α-androstan- 3-one (11,R$_1$=cyclo C$_6$H$_{11}$). The product was prepared in 52% yield and NMR spectro-scopy analysis gave a (4:1) mixture of two conformers, M.P. 144–146 ° C.; $^1$H NMR (CDCl$_3$): δ 0.70 (s, 1.5H), 0.77 (s, 1.5H), 0.85 (s,1.5H),0.87(s, 1.5H), 0.81–1.41 (m, 12H), 1.44–1.83 (m, 13H), 1.90–2.04 (m, 2H), 2.40 (dd,J =4.6, 9.3 Hz, 2H), 2.90 (s, 3H), 2.99 (dd,J=3.2, 12.4 Hz, 1H),3.16 (t,J=9.7, 9.9 Hz, 0.5H), 3.70–3.82 (m, 0.5H), 4.28 (t,J=9.6, 9.9 Hz, 0.5H), 8.30 (s, 0.5H), 8.38 (s, 0.5H). $^{13}$C NMR (CDCl$_3$): δ 170.7, 163.5, 163.1, 77.2, 66.3, 65.7, 61.9, 55.4, 54.4, 52.4, 52.1, 51.4 44.7, 43.1, 37.2, 36.8, 36.5, 34.2, 34.1, 33.7, 32.9, 30.9, 30.6, 29.8, 29.7, 29.3, 29.1, 29.0, 27.9, 26.9, 26.2, 26.0, 25.4, 25.3, 23.2, 22.9, 20.7, 20.5, 13.0, 12.6, 12.4; HRMS: calcd for C$_{26}$H$_{42}$N$_2$O$_2$, 414.3246 found 414.3270.

EM 402: 17β-(N-n-Hexyl-N-formamido)-4-methyl-4-aza-5α-androstan-3-one (11,R$_1$=C$_6$H$_3$). The product was prepared in 70 % yield. The NMR analysis gave a mixture of two conformers, M.P. 101°–103° C., $^1$H NMR (CDCl$_3$): δ 0.68 (s, 3H), 0.86 (s,3H), 0.77–1.09 (m, 6H), 1.22–1.42 (m, 10H), 1.43–1.57 (m, 2 H), 1.60–1.82 (m, 5H), 1.89–2.03 (m, 4H), 2.38–2.43 (m, 2H), 2.89 (s, 3H), 2.97–3.03 (dd, 1H,J=12.4, 3.2 Hz), 3.18–3.28 (m, 2.4H), 4.12 (t,0.2H,J=10 Hz), 8.14 (s, 0.8H),8.2 (s,0.2H); $^{13}$C NMR (CDCl$_3$): δ 170.57, 164.49, 162.97, 68.55, 65.58, 61.99, 51.95, 51.66, 51.26, 46.72, 45.66, 44.32, 44.22, 37.24, 36.8, 36.37, 34.07, 32.83, 32.43, 31.32, 29.64, 29.19, 29.04, 28.95, 28.47, 26.64, 26.35, 25.15, 24.34, 23.23, 22.84, 22.49, 20.51, 13.92, 12.32; HRMS: calcd for C$_{26}$H$_{44}$O$_2$N$_2$, 416.3382, found, 416.3355.

EM 405: 17β-(N-iso-Amyl-N-formamido)-4-methyl-4-aza-5α-androstan-3-one (11, R$_1$=iso-C$_5$H$_{11}$). The product was prepared in 66% yield. The NMR analysis gave a (4:1) mixture of two conformers, M.P. 87°–89° C., $^1$H NMR (CDCl$_3$): δ 0.67 (s, 3H), 0.77–1.06 (m, 12H), 1.21–1.57 (m, 10H), 1.71–1.80 (m, 4H), 1.82–1.97 (m, 3H), 2.38–2.43 (m, 2H), 2.89 (s, 3H), 2.97–3.01 (dd, 1H, J=12.4, 3.2 Hz), 3.20–3.29 (m, 1.8H), 4.16 (t, 0.2H,J=10 Hz), 8.13 (s, 0.8H), 8.2 (s, 0.2H); $^{13}$C NMR (CDCl$_3$): δ 170.57, 164.46, 162.91, 68.49, 65.58, 51.92, 51.63, 44.19, 42.72, 37.19. 36.80, 36.35, 34.07, 32.81, 29.64, 29.19, 29.04, 28.93, 26.28, 25.92, 25.15, 24.27, 22.84, 22.43, 20.51, 12.77, 12.32; HRMS: calcd for C$_{25}$H$_{42}$O$_2$N$_2$, 402.3245, found, 402.3230.

EM 407: 17β-(N-1-Ethylpropyl-N-formamido)-4-methyl-4-aza-5α-androstan-3-one (11, R=iso-C$_5$H$_{11}$). The product was prepared in 50% yield and the NMR analysis gave a (2.33:1) mixture of two conformers, M.P. 111°–113° C., $^1$H NMR (CDCl$_3$): δ 0.74–1.2 (m, 15H), 1.24–1.84 (m, 17H), 1.95–2.1 (m, 2 H),2.41–2.42 (m, 2H), 2.91 (s, 3H), 2.99–3.1 (m, 1.7H), 3.95 (t, 0.3H,J=10 Hz), 8.24 (s, 0.3H), 8.48 (s, 0.7H); $^{13}$C NMR (CDCl$_3$): δ 170.60, 163.88, 163.46, 66.28, 65.74, 65.62, 63.81, 52.85, 52.02, 51.89, 51.77, 44.94, 43.17, 37.24, 36.39, 34.22, 32.89, 29.75, 29.66, 29.07, 29.01, 28.89, 28.56, 28.47, 26.19, 25.32, 25.22, 23.25, 23.05, 22.98, 20, 78, 20.57, 13.25, 13.07, 12.36, 11.79, 11.44, 10.62; HRMS: calcd for C$_{25}$H$_{42}$O$_2$N$_2$, 402.3246, found 402.3265.

EM 422: 17β-(N-iso-Butyl-N-formamido)-4-methyl-4-aza-5-androstan-3-one (11, R$_1$=iso-C$_4$H$_9$). The product was prepared in 90% yield and the NMR analysis gave a (4:1) mixture of two conformers, M.P. 52°–54° C., $^1$H NMR (CDCl$_3$): δ 0.67 (s, 3H), 0.85 (s, 3H), 0.68–1.15 (m, 9H), 1,21–1.38 (m, 6H) 1.5–1.79 (m, 6H), 1.81–1.99 (m, 3H), 2.38–2.42 (m, 2H), 2.88 (s, 3H),2.94– 3.02 (dd, 1H,J=12.4, 3.3 Hz), 3.1–3.15 (dd, 0.2H,J=13.2, 5.7 Hz),3.23 (t, 0.8, J =0.8H), 3.32–3.39 (dd, 0.8H,J=13.2, 6.6 Hz), 4.05 (t, 0.2H, J=10 Hz), 8.15 (s, 0.2H), 8.29 (s, 0.8H); $^{13}$C NMR (CDCl$_3$): δ 170.57, 164.66, 162.82, 69.18, 65.57, 52.26, 51.89, 51.83, 51.23, 45.99, 44.25, 37.16, 36.34, 32.81, 29.04, 28.92, 28.03, 27.12, 26.76, 25.12, 24.94, 23.05, 22.81, 20.17, 19.96, 19.78, 12.84, 12.33; HRMS: calcd for C$_{24}$H$_{40}$N$_2$O$_2$, 388.3089, found, 388.3069.

EM 423:17β-(N-n-propyl-N-formamido)-4-methyl-4-aza-5α-androstan-3-one (11, R$_1$=C$_3$H$_7$). The product was prepared in 82% yield and the NMR analysis gave a (4.5:1) mixture of two conformers, M.P. 127°–129° C.; $^1$H NMR (CDCl$_3$) δ 0.65 (s, 3H), 0.83 (s, 3H), 0.69–1.13 (m, 6H), 1.19–1.81 (m, 13H), 1.86–2.0 (m, 3H), 2.35–2.4 (m, 2H), 2.86 (s, 3H), 2.94–3.0 (dd, 1H,J=12.4,3.2 Hz), 3.10–3.28 (m, 1.82H ), 4.1 (t, 0.18H,J=10 Hz), 8.11 (s, 0.82H), 8.17 (s, 0.18H); $^{13}$C NMR (CDCl$_3$) δ 170.51, 164.43, 162.99, 68.51, 65.52, 51.89, 51.62, 48.30, 45.82, 44.17, 36, 32, 34.03, 32,78, 29.58, 28.98, 28.89, 25.11, 24.31, 22.78, 21.61, 20,47, 12.27, 11.24; HRMS: calcd for C$_{23}$H$_{38}$O$_2$N$_2$, 374.2933, found 374.2903.

EM-436: 17β-(N-Benzyl-N-formamido)-4-methyl-4-aza-5α-androstan-3-one (11, R$_1$=CH$_2$C$_6$H$_5$). The product was prepared in 80% yield. The NMR analysis gave a mixture of two conformers (4.88:1), m.p. 89°–91° C., IR v cm$^{-1}$ (KBr): 1640, 1610; $^1$H NMR (CDCl$_3$): δ 0.74 (s, 3H), 0.85 (s, 3H), 2.37–2.42 (m, 2H), 2.87 (s, 3H), 2.95–3.0 (dd, 1H,J=12.5, 3.4 Hz), 3.28 (t, 0.8H,J=9.8 Hz), 4.18 (t, 0.2H,J=9.7 Hz), 4.4 (d,0.8H$_a$,J=15.5 Hz),4.5 (d,0.4H,J=3.8 Hz), 4.79 (d, 0.8H$_b$, J=15.5 Hz), 7.1–7.3 (m, 5H), 8.28 (s, 0.2H), 8.42 (s, 0.8H); $^{13}$C NMR (CDCl$_3$): δ 170.38, 165.17, 162.93, 138.76, 137.38, 128.55, 128.34, 127.27, 126.93, 125.93, 68.01, 65.42, 62.67, 51.80, 51.63, 51.20, 50.36, 47.28, 45.81, 44.11, 37.39, 37.06, 36.29, 34.04, 32.75, 29.61, 29.49, 28.87, 25.04, 24.65, 23.29, 22.72, 20.54, 12.95, 12.41, 12.23; HRMS: calcd for $C_{27}H_{38}O_2N_2$, 422.2933, found, 2.2924.

EXAMPLE 4

Preparation of 17β-(N-methyl-N-formamido)-4-methyl-4-aza-5α-androst-1-ene-3-one (17)

Preparation described in scheme 2

Preparation of 17β(N-methyl-N-formamido)-4-methyl-4-aza-5α-androst-1-ene-3-one (17, R$_1$=CH$_3$, EM 314). The following method is representative. Bis(trimethylsilyl)trifluoroacetamide (0.305 g, 1.185 mmol) was added to the mixture of formamide 11, R$_1$=CH$_3$ (EM 316) (0.10 g, 0.289 mmol) and 2,3-dichloro-5,6-dicyano-1,4-benzoquinone (0.066 g, 0.289 mmol) in dioxane (4 mL) under nitrogen. After 4 h at 25° C., the contents were heated at 110° C. for 24 h. The resulting dark red solution was pour into the stirred mixture of methylene chloride (6 mL) and 1% aqueous sodium bisulphite solution (1.8 mL). The heterogeneous mixture was filtered. The dark red organic layer was washed with 2 mL of 2N HCl followed by brine, dried and concentrated. The crude mixture was purified by column chromatography to give 41 mg of the product 17 R$_1$=CH$_3$ (EM 314) (41%); $^1$H NMR (CDCl$_3$): δ 0.72 (s, 3H (78%)), 0.74 (s, 3H(22%)), 0.86–2.15 (m, 15H), 0.89 (s, 3H(22%)),0.91 (s,3H(78%)), 2.89 (s, 3H), 2.93 (s, 3H), 3.27–3.36 (m, 2H), 5.82–5.85(m, 3H), 6,65 (d, 1H,J= 11 Hz), 8.14–8.24 (m, 1H); HRMS: calcd for $C_{21}H_{32}N_2O_2$, 344.2463; found 344.2426.

SCHEME 2

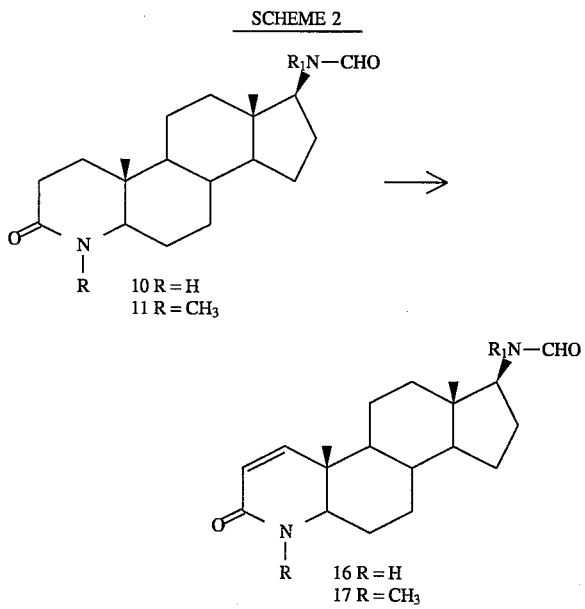

-continued
SCHEME 2

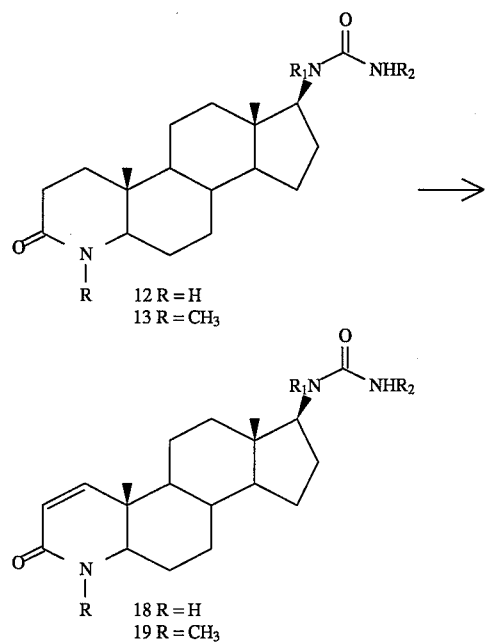

EXAMPLE 5

By analogous methods to those described in example 4, the compounds 16 (i.e. EM 346), 18 and 19 (i.e. EM 420) were synthesized using the formamide 10 or the ureas 12 and 13 as starting material.

EXAMPLE 6

Preparation of 17β-N-(1N-cyclopropyl-2N-phenylurea)-4-methyl 4-aza-5α-androstan-3-one (13, R$^1$=C$_3$H$_5$, R$^2$=C$_6$H$_5$, EM 374)

Preparation described in scheme 1

Preparation of 17β-N-(1N-cyclopropyl-2N-phenylurea)-4-methyl-4-aza-5α-androstan-3-one (13, R$_1$=cyclo C$_3$H$_5$, R$^2$=C$_6$H$_5$, EM 374). The following method is representative. To a solution of compound 9 (R$_1$, cyclo C$_3$H$_5$) (220 mg, 0.64 mmol) in THF (100 mL) was added N-methylmorpholine (0.107 mL, 0.975 mmol) followed by phenylisocyanate (0.1 mL, 0.9 mmol) at 0° C. under argon. The mixture was stirred overnight at 0° C. to room temperature. The mixture was diluted with ethyl acetate and washed twice with 2N HCl, dried and solvent removed to give the crude product which was purified by column to give the pure product 13 (EM 374) (210 mg, 73%); $^1$H NMR (CDCl$_3$): δ 0.74–1.11 (m, 6H), 0.8 (s, 3H), 0.86 (s, 3H), 1.23–2.06 (m, 14H), 2.34–2.65 (m, 4H), 2.9 (s, 3H), 2.99 (dd, 1H, J=4, 13 Hz), 4.06 (t, 1H,J=9.5 Hz), 7.0–7.42 (m, 5H); $^{13}$C NMR (CDCl$_3$): δ 170.72, 157.19, 139.09, 128.81, 122.77, 119.49, 65.63, 52.04, 51.10, 45.57, 38.08, 36.35, 34.22, 32.79, 29.70, 29.02, 27.79, 25.244, 23.43, 23.05, 20.72, 13.73, 12.35, 12.01, 9.96.

EXAMPLE 7

By analogous methods to those described in example 6, the following compounds were synthesized.

EM 373: 17β-N-(1N-cyclopropyl-2N-methylurea)-4-methyl-4-aza-5α-androstan-3-one (13, $R_1$=cyclo $C_3H_5$, $R_2$=$CH_3$). The product was prepared in 68% yield, $^1H$ NMR (CDCl$_3$): δ 0.71 (s, 3H), 0.82 (s, 3H), 1.94–198 (dd, 1H, J=12.6, 3.4 Hz), 2.28–2.33 (m, 1H), 2.35–2.40 (dd, 2H,J= 9.5, 4.8 Hz), 2.5–2.53 (q, 1H,J=10.36 Hz),2.76 (d, 3H,J=4.8 Hz), 2.87 (s, 3H),2.95–3.01 (dd, 1H,J=12.5, 3.4 Hz), 3.9 (t, 1H,J=10 Hz), 5.29 (q, 1H,J=5 Hz); $^{13}C$ NMR (CDCl$_3$): δ 170.66, 160.86, 67.74, 65.58, 52.01, 51.05, 45.16, 37.98, 36.31, 34.16, 32.75, 29.66, 28.96, 27.37, 25.21, 23.32, 22.94, 20.68, 13.61, 12,29, 11.43, 9.51; MS: m e (% rel. int.) 344 ($M^+$-57).

EM 392: 17βN-(1N-cyclopropyl-2N-ethylurea)-4-methyl-4-aza-5α-androstan-3-one (13, $R_1$=cyclo-$C_3H_5$, $R^2$=$C_2H_5$). The product was prepared in 78% yield, $^1H$ NMR (CDCl$_3$): δ 0.70 (s, 3H), 0.81 (s, 3H), 1.08 (t, 3H,J=7 Hz), 1.94 (dd, 1H,J=12.4, 3.2 Hz), 2.25–2.31 (m, 1H), 2.36 (dd, 1H,J=9.5, 4.8 Hz), 2.42–2.57 (q, 1H,J=1 0 Hz), 2.86 (s, 3H), 2.95–3.19 (dd, 1H,J=12.5,3.4 Hz), 3.20–3.23 (m, 2H), 3.9 (t, 1H,J=10 Hz), 5.27 (t, 1H,J=5 Hz); $^{13}C$ NMR (CDCl$_3$) δ 170.60, 160.03, 67.50, 65.55, 51.95, 50.96, 45.31, 37.95, 36.26, 35.27, 34.10, 32.70, 29.61, 28.92, 27.18, 25.17, 23.28, 22.90, 20.64, 15.47, 13.58, 12.26, 11.64, 9.57; HRMS: calcd for $C_{25}H_{41}N_3O_2$, 415.319, found, 415.318.

EM 408: 17βN-(1N-methyl-2N-phenylurea)-4-methyl-4-aza-5α-androstan-3-one (13, $R_1$=$CH_3$, $R_2$=$C_6H_5$). The product was obtained in 87% yield, $^1H$ NMR (CDCl$_3$): δ 0.73 (s, 3H), 0.86(s, 3H), 2.4 (dd, 2H,J =9.5, 4.7 Hz), 2.90 (s, 3H), 2.96 (s, 3H), 2.96–3.0 (dd, 1H,J=12.5, 3.4 Hz), 4.24 (t, 1H,J=10 Hz), 6.53 (s, 1H), 6.98 (t, 1H,J=7 Hz), 7.24 (t, 2H,J=7 Hz),7.36 (d, 2H, J=7 Hz); $^{13}C$ NMR (CDCl$_3$): δ 170.66, 156.37, 139.24, 128.69, 122.70, 119.79, 65,55, 63.96, 51.92, 51.17, 44.91, 37.35, 36.34, 33.92, 32.75, 31.58, 29.66, 29.03, 28.95, 25.19, 23.11, 20.50, 13.10, 12.30; HRMS: calcd for $C_{27}H_{39}N_3O_2$, 437.2804, found, 437.2823.

EXAMPLE 8

Preparation of 17βN-(1N-cyclopropyl-2N-methylthiourea)-4-methyl- 4-aza5α-androstan-3-one (15, EM 379)

The preparation is analogous to the preparation of compounds 13 in example 6 (see scheme 1), but using phenylisothiocyanate as reagent in the step converting compound 9 to compound 15.

EXAMPLE 9

Preparation of 17α-allyl-17β-hydroxy-4-methyl-4-aza-5α-androstan- 3-one (21, $R_3$=$C_3H_5$, EM 322).

Preparation described in scheme 3

Preparation of 17α-allyl-17β-hydroxy-4-methyl-4-aza-5αandrostan-3-one (21, $R_3$=$C_3H_5$, EM 322). The following method is representative. To a solution of compound 7 (see scheme 1) (0.1 g, 0.328 mmol) in THF (10 mL) was added allylmagnesium bromide (394 μL, 0.394 mmol) at –78° C. After addition the contents were stirred for 1 h and workup as usual to provide the crude product which was purified by column chromatography to give the pure product EM 322 (77 mg, 67%); $^1H$ NMR (CDCl$_3$): δ 0.68–1.0 (m, 2H), 0.84 (s, 6H), 1.14–1.66 (m, 11H), 1.77–2.06 (m, 5H), 2.14–2.2 (m, 1H), 2.28–2.36 (m, 1H), 2.42–2.48 (m, 2H), 2.86 (s, 3H), 2.94–2.99 (dd, 1H,J=4, 13 Hz), 5.14 (dd, 1H,J=17,2 Hz), 5.2 (dd, 1H, 13,2 Hz), 5.91–6.06 (m,1H);$^{13}C$ NMR (CDCl$_3$): δ 170.70, 134.85, 118.99, 82.13, 65.70, 51.91, 50.13, 46.33, 41.75, 36.45, 35.14, 34.78, 32.94, 31.63, 29.95, 29.03, 25.31, 23.55, 20.77, 14.55, 12.37; HRMS: calcd for $C_{22}H 35NO_2$, 345.2668; found, 345.2658.

SCHEME 3

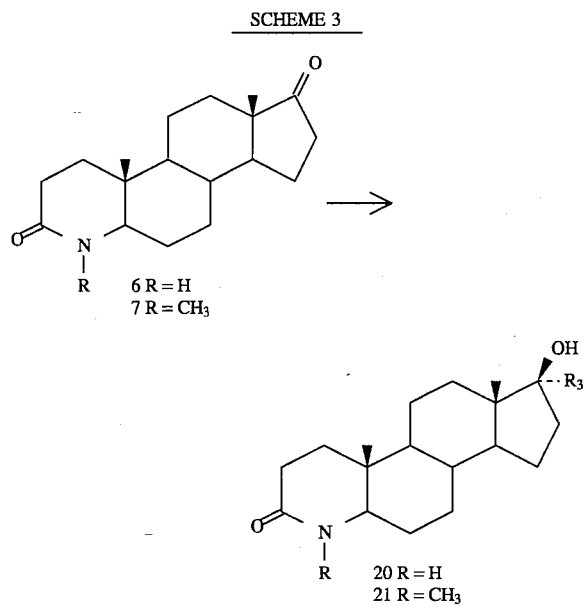

6 R = H
7 R = $CH_3$

20 R = H
21 R = $CH_3$

EXAMPLE 10

Preparation of 17α-propyl-17β-hydroxy-4-methyl-4-aza-5α-androstan-3-one (21, $R_3$=$C_3H_7$, EM 378). Same preparation as the preparation of compounds 21 in example 9, but using propylmagnesium bromide instead of allylmagnesium bromide as reagent.

EXAMPLE 11

Preparation of 17α-allyl-17β-hydroxy-4-aza-5α-androstan-3-one (20, $R_3$=$C_3H_5$, EM 441)

Same preparation than the preparation of compounds 21 in example 9 in using the compound 6 as starting material.

EXAMPLE 12

Synthesis of 17α-(4-bromo-butynyl)-17β-hydroxy-4-aza-5α- androstane-3-one (24, x=2, P=Br, EM 465) (scheme 4)

Preparation described in scheme 1 and scheme 4

Preparation of 17β-hydroxy-4-aza-androst-5-ene-3-one (2). Referring first to sheme 1, in a pressure apparatus , $NH_3$ was bubbled till saturation to a mixture of the seco acid 1 (6.0 g, 18 mmol) in ethylene glycol (60 mL) at room temperature. The clear yellowish solution was heated gradually (3° C./min) up to 180° C. and held at this temperature for 1 h. The reaction mixture was cooled to 10° C. and water (80 mL) was added with stirring. The solid was filtered, washed with water (20 mL) and dried to give 4.5 g of 2.

Preparation of 4-aza-5α-androstan-3,17-dione (6). A solution of the compound 2 (160 g, 0.5 mol) in acetic acid (500 mL) was hydrogenated at 60 psi using PtO2 (15 g) as catalyst at 60° C. for 60 min After cooling and filtering, the catalyst was washed with acetic acid and the solvent removed. The residue dissolved in methylene chloride was washed with 1N sulfuric acid, brine, saturated sodium bicarbonate, and brine. The organic phase was dried, filtered, and evaporated. The residue was chromatographed on silica gel. Elution with ethyl acetate/hexane gave crystalline compound which was treated with 3% methanolic sodium hydroxide solution at reflux for 90 min. After usual work up the obtained residue was dissolved in acetone (500 mL) cooled to 0° C. and Jones' reagent was added (8N-chromic acid solution, 65 mL). After 15 min., isopropanol was added and the mixture was concentrated under vacuo. Water was added and the mixture was extracted with ethyl acetate. The organic layers were washed with brine, dried and evaporated to dryness. The chromatography on silica-gel of the residue with ethyl acetate/hexane as eluent gave the aza-ketone 6 (152 g) of which structure was determined by spectroscopic mean.

17α-(4-tetrahydropyranyloxy-butynyl)-17β-hydroxy-4-aza-5α-androstan-3-one (22,x=2). Referring now to scheme 4, to anhydrous THF (140 mL) at –60° C. was added methyl lithium (1.4 M, 100 mL) and a solution of 4-tetrahydropybromo-butynyl)-17β-hydroxy-4-methyl-4-aza-5α -androstane-3-one (25,x=2,P=Br,EM 321) was prepared.

Preparation of 17α-(4-iodobutynyl)-17β-hydroxy-4-methyl-4-aza-5α-androstan-3-one (25, x=2, P=I, EM 320). To a mixture of 17α-(4-bromobutynyl)-17β-hydroxy- 4-methyl-4-aza-5α-androstan-3-one (25, x=2, P=B$_r$, EM 321) (200 mg, 0.471 mmol) in acetone (16 mL) was added sodium iodide (92 mg, 0.6132 mmol) and the mixture was refluxed for 12 h. Removal of acetone and usual workup provided the crude product which was purified by column chromatography to give the pure product (EM 320) (137 mg, 60%); $^1$H NMR (CDCl$_3$): δ 0.83 (s, 3H), 0.88 (s, 3H), 2.41–2.46 (m, 2H), 2.83 (t, 2H, J=6.84 Hz), 2.91 (s, 3H), 3.0–3.06 (dd, 1H,J=3.4, 12.5 Hz), 3.24 (t, 2H,J=7.1 Hz); HRMS: calcd for C$_{23}$H$_{34}$INO$_2$, 483.1635; found, 483.1634.

SCHEME 4

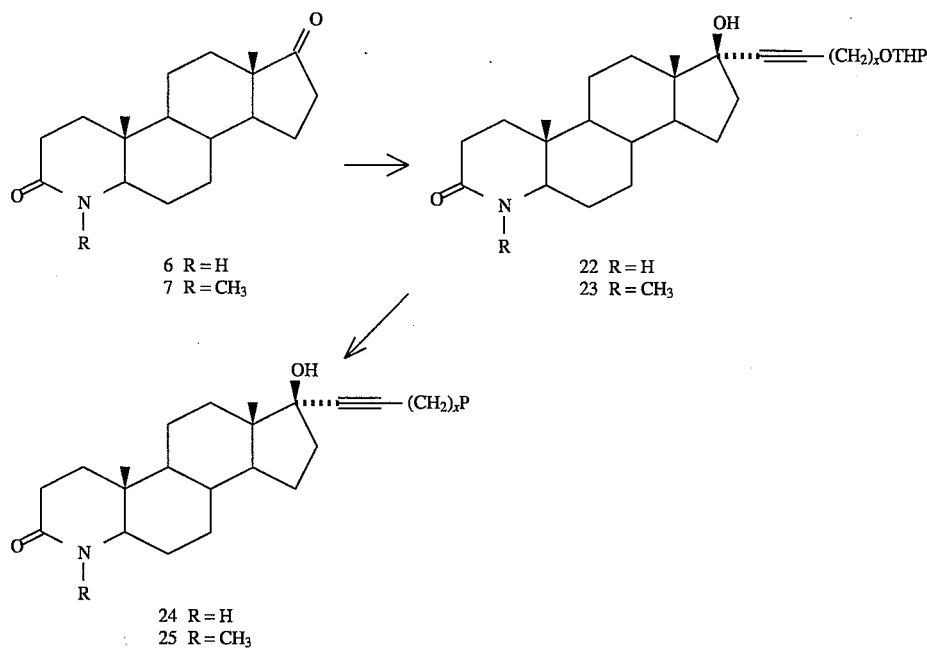

ranyloxybutyne (21.6 g, 140 mmol).To this mixture warmed up to room temperature, stirred for 2h, and cooled to –60° C. was added dropwise a solution of above aza-ketone 6 (9.6 g, 30 mmol) in THF (350 mL), and the mixture was warmed up to room temperature and stirred for 16h. After usual work up, the compound 22 (x=2) was purified by silica-gel chromatography and its structure determined by spectroscopic mean. In a similar fashion, 17α-(4-tetrahydropyranyloxybutynyl)-17β-hydroxy-4-methyl-4-aza-5α-androstan-3-one (23, x=2) was prepared.

17α-(4-bromo-butynyl)-17β-hydroxy-4-aza-5α-androstane-3-one (24, P=Br, x=2, EM 465). To a solution of aza-diol 24, (P=OH) (179 mg, 0,5 mmol) obtained by acidic hydrolysis of the compound 22, and triphenylphosphine (262 mg, 1 mmol) in methylene chloride (15 mL) at 0° C. was added CBr$_4$ (249 mg, 1 mmol)and the mixture was stirred for 2 h at room temperature. the solvent was removed and the compound 24 (P=Br, x=2 EM 465) was purified by flash silica-gel chromatography and this structure determined by spectroscopic mean. In a similar fashion, 17α-(4-

EXAMPLE 13

In a similar fashion, to Example 12, the following compounds described in Table IV are prepared using different tetrahydropyranyloxy-alkynes and different carbon tetrahalides.

TABLE IV

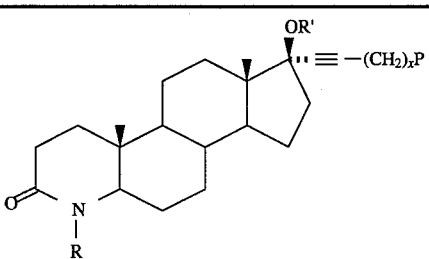

| | R | R' | x | p |
|---|---|---|---|---|
| EM 501 | H | H | 2 | Cl |
| EM 502 | CH$_3$ | COC$_6$H$_5$ | 2 | Cl |
| EM 503 | CH$_3$ | H | 2 | Cl |
| EM 448 | H | H | 2 | I |
| EM 320 | CH$_3$ | H | 2 | I |
| EM 471 | H | H | 3 | I |
| EM 358 | H | H | 3 | Br |

EXAMPLE 14

Preparation of 17β-(N-n-butyl-N-formamido)-4, 6-dimethyl-4-aza-5α-androstan-3-one (31, EM 548)

Preparation described in Scheme 5.

Preparation of 17β-acetoxy-6α-methyl-4-androsten-3-one (30). Testosterone (50 g) (Schering A. G. Germany) was treated in an apparatus equipped with a Dean-Stark, distillation apparatus, by diethylene glycol in toluene in the presence of a catalytic amount of p-toluenesulfonic acid at reflux for 16 h. The resulting ketal 26 was oxidized by monoperoxyphtalic acid, magnesium salt (Aldrich Chem. Comp, Inc. Milwaukee, Wis. USA) in iso-propanol at 50° C. for 1 h. After removal of the solvent and crystallization the mixture of epoxyde 27 was heated at reflux with large excess methyl magnesium iodide in tetrahydrofuran for 18 h. The 6β-methyl ketal 28 was deprotected by standing overnight at room temperature with a mixture of acetone/water (9:1). The hydroxy ketone 29 thus obtained was mono dehydrated by heating in a mixture of 0.1N sodium hydroxide in methanol and the 17β-hydroxyl was acetylated by usual manner (acetic anhydride/pyridine). The 6-methyl enone 30 was thus obtained (27 g) and characterized by spectroscopy.

17β-(N-n-butyl-N-formamido)-4, 6-dimethyl-4-aza-5α-androstan-3-one (31, EM 548). The 6-methyl enone 30 is transformed into 17β-(N-n-butyl-N-formamido)-4, 6-dimethyl- 4-aza-5α-androstan-3-one (31, EM 548) by a process analogous to the process described in the example 1 for conversion of compound testosterone acetate to compound 11.

SCHEME 5

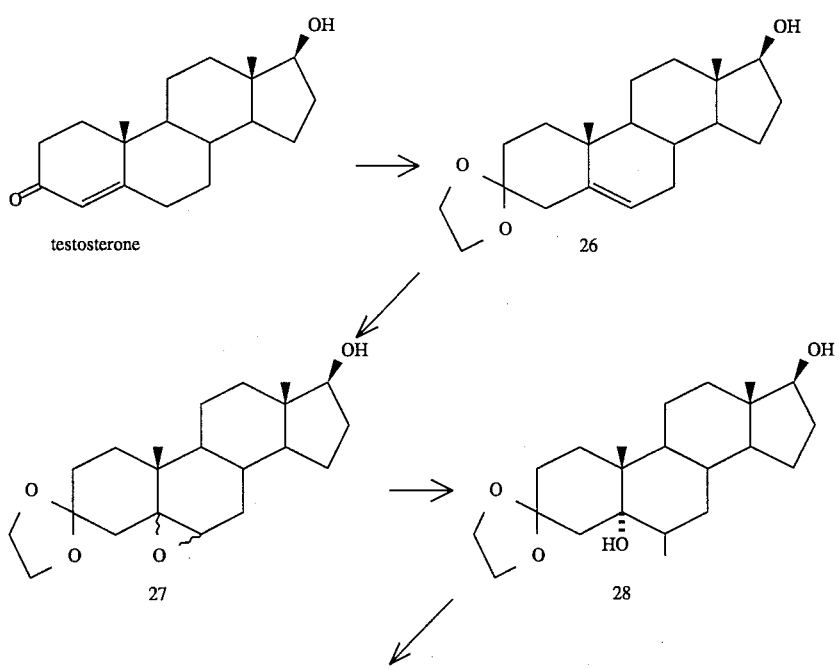

-continued
SCHEME 5

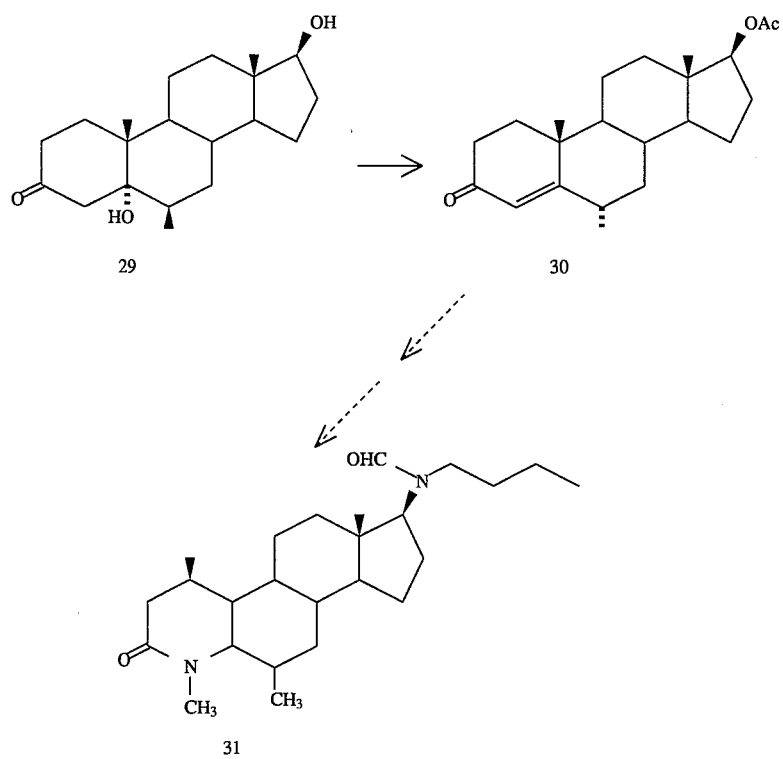

EXAMPLE 15

Preparation of 17β-(N-alkyl-N-formamido)-4-methyl-7α- hydroxyalkyl-4-aza-5α-androstan-3-one (34)

Synthesis is described in scheme 6

The following method is representative. The commercial 17β-acetoxy-4, 6-androstadien-3-one 32 (Steraloids Inc. Wilton, N.H., USA) is treated by an 1.5 excess of TBDMSO(CH$_2$)$_x$Cu(CN)Li (prepared from TBDMSO(CH$_2$)$_x$I,t-BuLi and CuCN) in ether and tetrahydrofuran in presence of trimethylsilyl chloride at −78° C. The mixture is heated to room temperature and usual work up is made. The resulting compound 33 is transformed into 17β-(N-alkyl-N-formamido)-4-methyl-7α-hydroxyalkyl-4-aza-5α-androstan-3-one (34) by a process similar to the process described in the example 1. The last step is the deprotection of the silyl group.

SCHEME 6

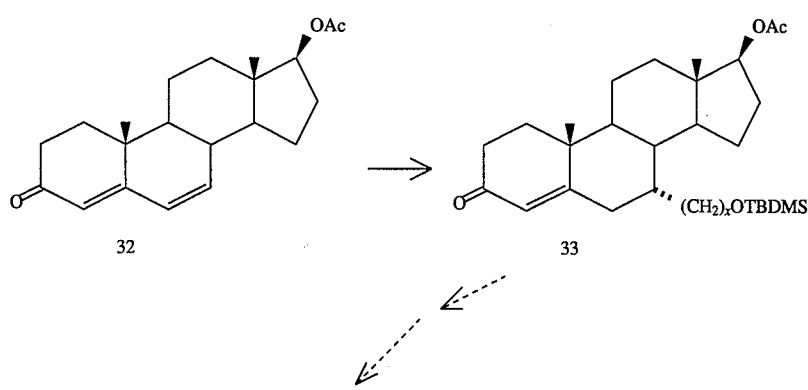

-continued
SCHEME 6

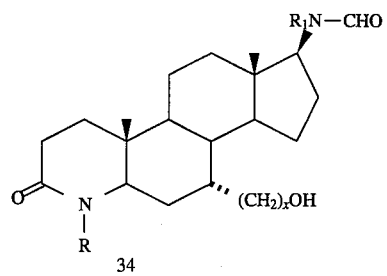

34

EXAMPLE 16

Preparation of alkylamide, alkylsulfamide and alkylphosphite derivatives of 17β-N-alkyl-4-methyl-4-aza-5α-androstan-3-one Synthesis is described in scheme 7

The compounds 8 or 9 prepared in accordance with scheme 1 are treated at room temperature by acyl chloride in tetrahydrofuran using a 2 fold excess of $K_2CO_3$ powder as base. After usual work up, the compounds 35 or 36 are obtained. The use of sulfonyl chloride instead of acyl chloride gives in the same conditions respectively the compounds 37 or 38, and the use of dialkyl chloro phosphate gives respectively the compounds 39 or 40.

EM 424: 17β-(N-n-butyl-N-acetamido)-4-methyl-4-aza-5α-androstan-3-one. The product was prepared in 85% yield. The NMR analysis gave a (1.85:1) mixture of two conformers, M.P. 152°–154° C., $^1$H NMR (CDCl$_3$): δ 0.67 (s, 1.95 H), 0.74 (s, 1.05H), 0.80–1.0 (m, 9H), 1.07–1.69 (m, 12H), 1.71–1.91 (m, 5H), 1.99–2.07 (m, 1H), 2.12 (s, 1.05H), 2.14 (s, 1.95H), 2.42–2.45 (m, 2H), 2.84–3.0 (m, 0.35H), 2.91 (s, 3H), 3.0–3.05 (dd, 1H,J=12.3, 3.2 Hz), 3.11–3.18 (m, 0.65H), 2.24–2.29 (m, 0.65H), 3.68–3.71 (m, 0.7H),4.49 (t, 0.65H,J=9.9 Hz); $^{13}$C NMR (CDCl$_3$): δ 171.43, 171.14, 170.54, 67.29, 65.53, 62.27, 51,05, 46, 36, 45.55, 44.55, 44.34, 37.10, 36.31, 33.96, 33.01, 32.75, 30.87, 29.67, 29.22, 28.98, 28.94, 25.18, 24.59, 23.65, 23.17, 22.70, 22.33, 20.49, 20.34, 20.04, 13.66, 12.94, 12.73, 12.29; HRMS: calcd for $C_{25}H_{42}N_2O_2$, 402.3246, found, 402.3234.

SCHEME 7

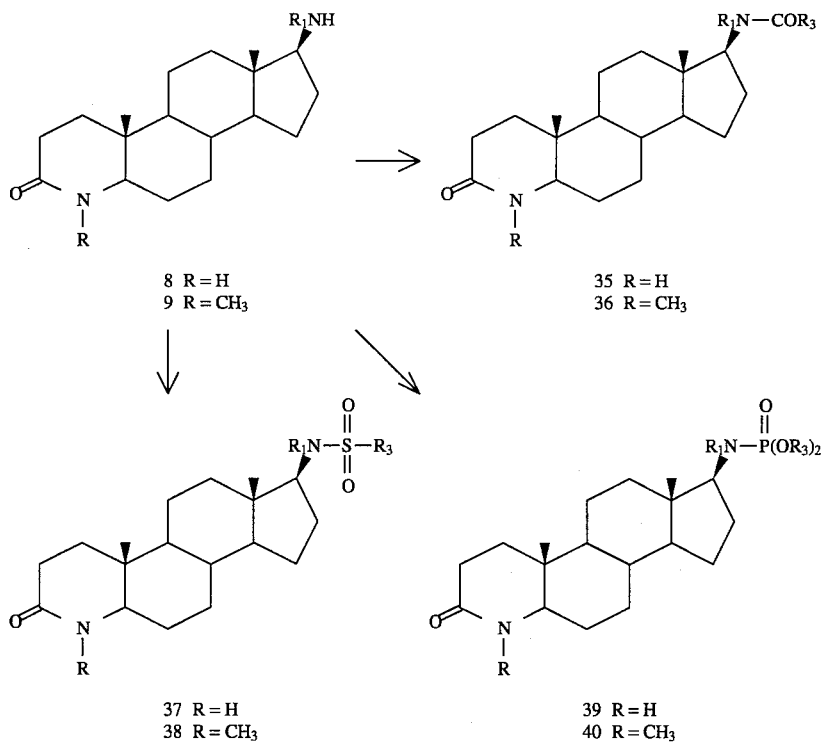

Additional examples of pharmaceutical compositions are set forth below:

EXAMPLE 17

Composition suitable for injection

| Ingredient | % by Weight of Total Composition |
|---|---|
| EM 378 (a 5α-reductase inhibitor) | 0.4 |
| Ethanol | 6.4 |
| NaCl | 0.8 |
| Water | 91.5 |
| Benzyl alcohol | 0.9 |

EXAMPLE 18

Topical lotion

| Ingredient | % by Weight of Total Composition |
|---|---|
| EM 402 (a 5α-reductase inhibitor) | 5.0 |
| Ethanol | 47.5 |
| Propylene glycol | 47.5 |

EXAMPLE 19

A tablet

| Ingredient | % by Weight of Total Composition |
|---|---|
| EM 378 (a 5α-reductase inhibitor) | 46.5 |
| Flutamide (an antiandrogen available from Schering Corp., New Jersey) | 46.5 |
| Gelatin | 2.0 |
| Lactose | 2.5 |
| Starch | 2.5 |

EXAMPLE 20

A topical lotion

| Ingredient | % by Weight of Total Composition |
|---|---|
| EM 402 (a 5α-reductase inhibitor) | 5.0 |
| EM 248 (an antiandrogen) | 5.0 |
| Ethanol | 45.0 |
| Propylene glycol | 45.0 |

The terms and descriptions used herein are preferred embodiments set forth by way of illustration only, and are not intended as limitations on the many variations which those of skill in the art will recognize to be possible in practicing the present invention as defined by the claims.

What is claimed is:

1. A pharmaceutical composition comprising a pharmaceutically acceptable diluent or carrier and a therapeutically effective amount of an inhibitor of testosterone 5α-reductase having the molecular formula:

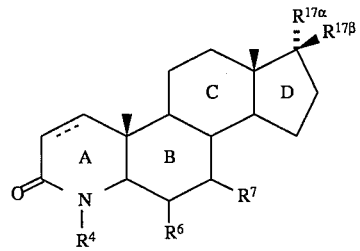

wherein the dotted line is an optional pi bond;

wherein $R^4$ is hydrogen or methyl;

wherein $R^6$ is a hydrogen or $C_1$–$C_3$ saturated or unsaturated hydrocarbon;

wherein $R^7$ is selected from the group consisting of hydrogen, $C_1$–$C_6$ alkyl, $C_1$–$C_6$ hydroxyalkyl, $C_1$–$C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing;

wherein $R^{17\alpha}$ is hydrogen or lower alkyl; and wherein $R^{17\beta}$ is tertiary amino or tertiary amido.

2. The pharmaceutical composition of claim 1, wherein $R^7$ is $C_2$–$C_6$ alkyl, $C_2$–$C_6$ alkenyl or $C_2$–$C_6$ alkynyl.

3. The pharmaceutical composition of claim 1, wherein $R^{17\alpha}$ is hydrogen.

4. The pharmaceutical composition of claim 1, wherein $R^{17\beta}$ is $N(R^{25})C(O)R^{26}$, Wherein $R^{25}$ is a $C_1$–$C_6$ saturated or unsaturated hydrocarbon and $R^{26}$ is hydrogen or lower alkyl.

5. The pharmaceutical composition of claim 4, wherein $R^{26}$ comprises cyclo lower alkyl.

6. The pharmaceutical composition of claim 1, wherein $R^4$ is methyl.

7. The pharmaceutical composition of claim 1, wherein $R^{17\beta}$ is —$N(R^{19})(R^{20})$ where $R^{19}$ is lower alkyl or haloalkyl and $R^{20}$ is lower alkyl.

8. The pharmaceutical composition of claim 4, wherein $R^{25}$ is selected from the group consisting of amyl, butyl, isobutyl and $C_3$–$C_6$ cycloalkyl.

9. A pharmaceutical composition comprising a pharmaceutically acceptable diluent or carrier and a therapeutically effective amount of an inhibitor of testosterone 5α-reductase having the molecular formula:

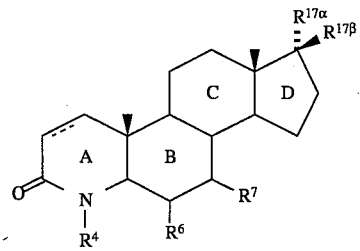

wherein the dotted line is an optional pi bond;

wherein $R^4$ is hydrogen or methyl;

wherein $R^6$ is a hydrogen or $C_1$–$C_3$ saturated or unsaturated hydrocarbon;

wherein $R^7$ is selected from the group consisting of hydrogen, $C_1$–$C_6$ alkyl, $C_1$–$C_6$ hydroxyalkyl, $C_1$–$C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing;

wherein $R^{17\alpha}$ is selected from the group consisting of $C_1$–$C_6$ alkyl, $C_1$–$C_6$ hydroxyalky, $C_1$–$C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing; and wherein $R^{17\beta}$ is hydrogen, hydroxy or a moiety converted to hydroxy in vivo.

10. The pharmaceutical composition of claim 9, wherein $R^7$ is $C_2$–$C_6$ alkyl, $C_2$–$C_6$ alkenyl, or $C_2$–$C_6$ alkynyl.

11. The pharmaceutical composition of claim 9, wherein $R^4$ is methyl.

12. The pharmaceutical composition of claim 9, wherein $R^{17\beta}$ is hydroxy and $R^{17\alpha}$ is selected from the group consisting of $C_1$–$C_6$ haloalkenyl, $C_1$–$C_6$ haloalkynyl, $C_3$–$C_6$ hydroxyalkenyl and $C_3$–$C_6$ hydroxyalkynyl.

13. The pharmaceutical composition of claim 12, wherein $R^{17\alpha}$ is unsaturated at the 1, 2 or 3 position and wherein said $R^{17\alpha}$ substituent includes a terminal halo or hydroxy.

14. A pharmaceutical composition comprising a pharmaceutically acceptable diluent or carrier and a therapeutically effective amount of an inhibitor of testosterone 5α-reductase having the molecular formula:

wherein the dotted line is an optional pi bond;

wherein $R^4$ is hydrogen or methyl;

wherein $R^6$ is a $C_1$–$C_3$ saturated or unsaturated hydrocarbon;

wherein $R^7$ is selected from the group consisting of hydrogen, $C_1$–$C_6$ alkyl, $C_1$–$C_6$ hydroxyalkyl, $C_1$–$C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing;

wherein $R^{17\alpha}$ is hydrogen or lower alkyl; and wherein $R^{17\beta}$ is selected from the group consisting of acyl, carboxamide, tertiary amino and tertiary amido.

15. The pharmaceutical composition of claim 14, wherein $R^{17\beta}$ is tertiary amino or tertiary amido.

16. A pharmaceutical composition comprising a pharmaceutically acceptable diluent or carrier and a therapeutically effective amount of an inhibitor of testosterone 5α-reductase having the molecular formula:

wherein the dotted line is an optional pi bond;

wherein $R^4$ is hydrogen or methyl;

wherein $R^6$ is a hydrogen or a $C_1$–$C_3$ saturated or unsaturated hydrocarbon;

wherein $R^7$ is selected from the group consisting of a $C_2$–$C_6$ hydroxyalkyl, $C_2$–$C_6$ haloalkyl, $C_2$–$C_6$ carbonylalkyl, $C_3$–$C_6$ epoxyalkyl and unsaturated analogs of the foregoing;

wherein $R^{17\alpha}$ is hydrogen or lower alkyl; and wherein $R^{17\beta}$ is selected from the group consisting of acyl, carboxamide, tertiary amino and tertiary amido.

17. The pharmaceutical composition of claim 16, wherein $R^{17\beta}$ is tertiary amino or tertiary amido.

18. A pharmaceutical composition comprising a pharmaceutically acceptable diluent or carrier and a therapeutically effective amount of an inhibitor of testosterone 5α-reductase of the formula:

wherein the dotted line is an optional pi bond;

wherein $R^4$ is hydrogen or methyl;

wherein $R^6$ is hydrogen or a $C_1$–$C_3$ hydrocarbon;

wherein $R^7$ is selected from the group consisting of hydrogen, a $C_1$–$C_6$ alkyl, $C_1$–$C_6$ hydroxyalkyl, $C_1$–$C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing;

wherein $R_a$ is selected from the group consisting of lower alkyl, and cycloalkyl;

wherein $R_b$ is selected from the group consisting of —$COR_c$, —$CONR_cR_d$, —$CSNR_cR_d$, —$SO_2R_c$, —$PO_3R_cR_d$ ($R_c$ and $R_d$ being hydrogen, lower alkyl or lower haloalkyl).

19. The pharmaceutical composition of claim 18, wherein $R^7$ is $C_2$–$C_6$ alkyl, $C_2$–$C_6$ alkenyl, or $C_2$–$C_6$ alkynyl.

20. A pharmaceutical composition comprising a pharmaceutically acceptable diluent or carrier and a therapeutically effective amount of at least one inhibitor of testosterone 5α-reductase having the molecular structure:

EM 401

17β-(N-n-Amyl-N-formamido)-4-methyl-4-aza-5α-androstan-3-one, and

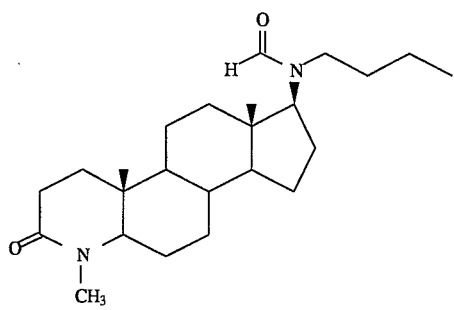

17β-(N-n-butyl-N-formamido)-4-methyl-4-aza-5α-androstan-3-one.

21. A pharmaceutical composition comprising a pharmaceutically acceptable diluent or carrier and a therapeutically effective amount of at least one inhibitor of testosterone 5α-reductase having the molecular formula:

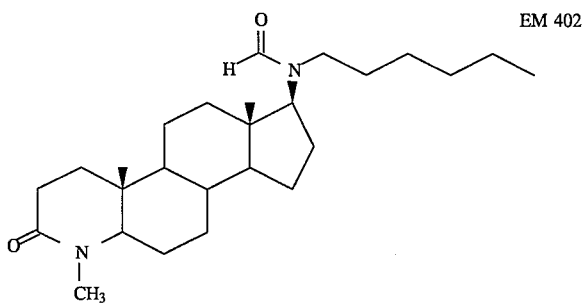

17β-(N-n-hexyl-N-formamido)-4-methyl-4-aza-5α-androstan-3-one.

22. A pharmaceutical composition comprising a pharmaceutically acceptable diluent or carrier and a therapeutically effective amount of at least one inhibitor of testosterone 5α-reductase selected from the group consisting of:

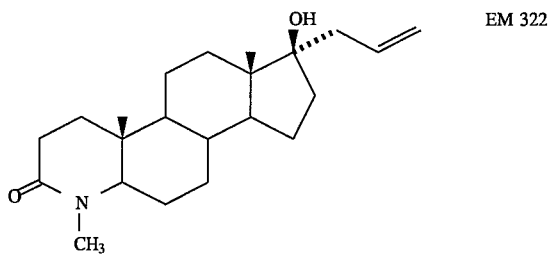

17β-allyl-17β-hydroxy-4-methyl-4-aza-5α-androstan-3-one and

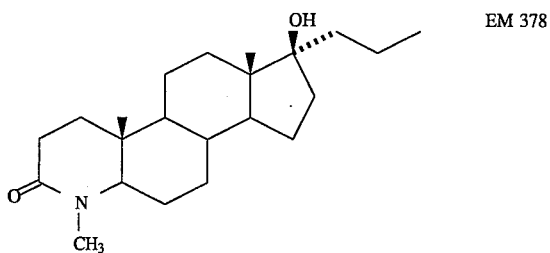

17α-propyl-17β- hydroxy-4-methyl-4-aza-5α-androstan-3-one.

23. A pharmaceutical composition comprising a pharmaceutically acceptable diluent or carrier and a therapeutically effective amount of at least one inhibitor of testosterone 5α-reductase having the molecular formula:

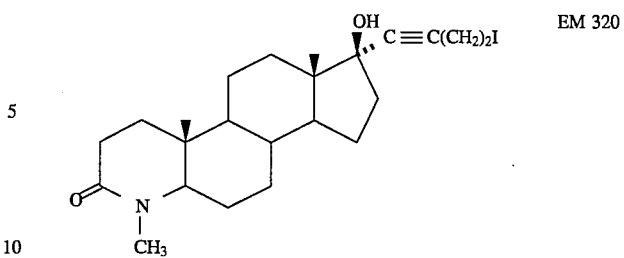

17α-(4-iodo-butynyl)-17β-hydroxy-4-methyl-4-aza-5α-androstane-3-one.

24. A method of inhibiting testosterone 5α-reductase activity in a patient in need of such inhibition, said method comprising administering to said patient a therapeutically effective amount of an inhibitor of testosterone 5α-reductase having the molecular formula:

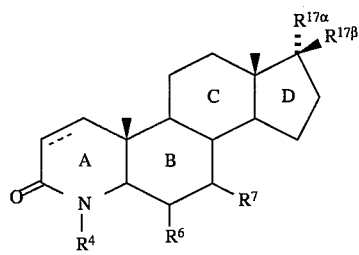

wherein the dotted line is an optional pi bond;
wherein $R^4$ is hydrogen or methyl;
wherein $R^6$ is a hydrogen or $C_1$-$C_3$ saturated or unsaturated hydrocarbon;
wherein $R^7$ is selected from the group consisting of hydrogen, $C_1$-$C_6$ alkyl, $C_1$-$C_6$ hydroxyalkyl, $C_2$-$C_6$ haloalkyl, $C_2$-$C_6$ carbonylalkyl, $C_3$-$C_6$ cyclopropylalkyl, $C_3$-$C_6$ epoxyalkyl and unsaturated analogs of the foregoing;
wherein $R^{17\alpha}$ is hydrogen or lower alkyl; and
wherein $R^{17\beta}$ is tertiary amino or tertiary amido.

25. The method of claim 22 wherein said inhibitor is administered by topical application to the skin.

26. The method of claim 25 wherein said patient is afflicted with a skin disease whose progress is aided by activation of androgen receptors, and wherein said topical application is for the treatment of said skin disease.

27. A method of inhibiting testosterone 5α-reductase activity in a patient in need of such inhibition, said method comprising administering to said patient a therapeutically effective amount of an inhibitor of testosterone 5α-reductase having the molecular formula:

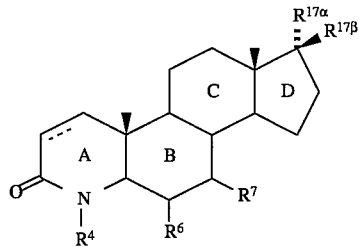

wherein the dotted line is an optional pi bond;
wherein $R^4$ is hydrogen or methyl;
wherein $R^6$ is a hydrogen or $C_1$-$C_3$ saturated or unsaturated hydrocarbon;

wherein $R^7$ is selected from the group consisting of hydrogen, $C_1$–$C_6$ alkyl, $C_1$–$C_6$ hydroxyalkyl, $C_1C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing;

wherein $R^{17\alpha}$ is selected from the group consisting of $C_1$–$C_6$ alkyl, $C_1$–$C_6$ hydroxyalky, $C_1$–$C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing; and wherein $R^{17\beta}$ is hydrogen, hydroxy or a moiety converted to hydroxy in vivo.

28. The method of claim 27 wherein said inhibitor is administered by topical application to the skin.

29. The method of claim 28 wherein said patient is afflicted with a skin disease whose progress is aided by activation of androgen receptors, and wherein said topical application is for the treatment of said skin disease.

30. A method of inhibiting testosterone 5α-reductase activity in a patient in need of such inhibition, said method comprising administering to said patient a therapeutically effective amount of an inhibitor of testosterone 5α-reductase having the molecular formula:

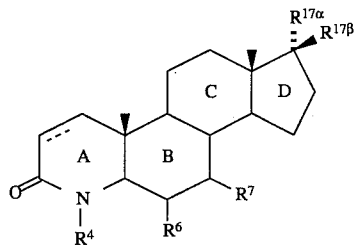

wherein the dotted line is an optional pi bond;
wherein $R^4$ is hydrogen or methyl;
wherein $R^6$ is a $C_1$–$C_3$ saturated or unsaturated hydrocarbon;
wherein $R^7$ is selected from the group consisting of hydrogen, $C_1$–$C_6$ alkyl, $C_{1-C6}$ hydroxyalkyl, $C_1$–$C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing;
wherein $R^{17\alpha}$ is hydrogen or lower alkyl; and
wherein $R^{17\beta}$ is selected from the group consisting of acyl, carboxamide, tertiary amino and tertiary amido.

31. The method of claim 30 wherein said inhibitor is administered by topical application to the skin.

32. The method of claim 31 wherein said patient is afflicted with a skin disease whose progress is aided by activation of androgen receptors, and wherein said topical application is for the treatment of said skin disease.

33. A method of inhibiting testosterone 5α-reductase activity in a patient in need of such inhibition, said method comprising administering to said patient a therapeutically effective amount of an inhibitor of testosterone 5α-reductase having the molecular formula:

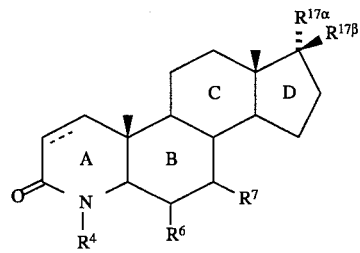

wherein the dotted line is an optional pi bond;
wherein $R^4$ is hydrogen or methyl;
wherein $R^6$ is a hydrogen or a $C_1$–$C_3$ saturated or unsaturated hydrocarbon;
wherein $R^7$ is selected from the group consisting of a $C_2$–$C_6$ alkyl, $C_2$–$C_6$ hydroxyalkyl, $C_2$–$C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing;
wherein $R^{17\beta}$ is hydrogen or lower alkyl; and
wherein $R^{17\beta}$ is selected from the group consisting of acyl, carboxamide, tertiary amino and tertiary amido.

34. The method of claim 33 wherein said inhibitor is administered by topical application to the skin.

35. The method of claim 34 wherein said patient is afflicted with a skin disease whose progress is aided by activation of androgen receptors, and wherein said topical application is for the treatment of said skin disease.

36. A method of inhibiting testosterone 5α-reductase activity in a patient in need of such inhibition, said method comprising administering to said patient a therapeutically effective amount of an inhibitor of testosterone 5α-reductase having the molecular formula:

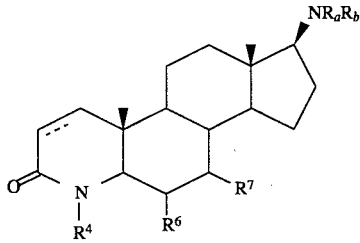

wherein the dotted line is an optional pi bond;
wherein $R^4$ is hydrogen or methyl;
wherein $R^6$ is hydrogen or a $C_1$–$C_3$ hydrocarbon;
wherein $R^7$ is selected from the group consisting of hydrogen, a $C_1$–$C_6$ alkyl, $C_1$–$C_6$ hydroxyalkyl, $C_1$–$C_6$ haloalkyl, $C_2$–$C_6$ carbonylalkyl, $C_3$–$C_6$ cyclopropylalkyl, $C_3$–$C_6$ epoxyalkyl and unsaturated analogs of the foregoing;
wherein $R_a$ is selected from the group consisting of lower alkyl, and cycloalkyl; and
wherein $R_b$ is selected from the group consisting of —$COR_c$, —$CONR_cR_d$, —$CSNR_cR_d$, —$SO_2R_c$, —$PO_3R_cR_d$ ($R_c$ and $R_d$ being hydrogen, lower alkyl or lower haloalkyl).

37. The method of claim 36 wherein said inhibitor is administered by topical application to the skin.

38. The method of claim 37 wherein said patient is afflicted with a skin disease whose progress is aided by activation of androgen receptors, and wherein said topical application is for the treatment of said skin disease.

* * * * *